(12) United States Patent
Ono et al.

(10) Patent No.: US 6,569,104 B2
(45) Date of Patent: May 27, 2003

(54) BLOOD VESSEL DETECTING APPARATUS

(75) Inventors: Shigeaki Ono, Utsunomiya (JP);
Shinya Tanaka, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 40 days.

(21) Appl. No.: 09/351,903

(22) Filed: Jul. 14, 1999

(65) Prior Publication Data

US 2002/0058874 A1 May 16, 2002

(30) Foreign Application Priority Data

Jul. 16, 1998 (JP) .......................................... 10-219696
Jul. 23, 1998 (JP) .......................................... 10-223635

(51) Int. Cl.⁷ ................................................ A61B 5/00
(52) U.S. Cl. ...................................... 600/504; 600/476
(58) Field of Search ................................ 600/478, 489, 600/564, 479, 480; 351/206, 209, 476

(56) References Cited

U.S. PATENT DOCUMENTS

| 4,951,670 A | | 8/1990 | Tanaka et al. | |
| 4,952,050 A | * | 8/1990 | Aizu et al. | .................. 351/206 |
| 5,031,623 A | | 7/1991 | Kohayakawa et al. | |
| 5,090,799 A | * | 2/1992 | Makino et al. | .............. 351/221 |
| 5,107,851 A | | 4/1992 | Yano et al. | |
| 5,129,400 A | * | 7/1992 | Makino et al. | .............. 351/206 |
| 5,141,303 A | * | 8/1992 | Yamamoto et al. | ......... 351/211 |
| 5,455,644 A | | 10/1995 | Yazawa et al. | |
| 5,615,683 A | | 4/1997 | Toge et al. | |
| 5,844,658 A | * | 12/1998 | Kishida et al. | .............. 351/206 |
| 5,894,337 A | | 4/1999 | Okinishi et al. | |
| 5,976,096 A | * | 11/1999 | Shimizu et al. | .............. 600/504 |

FOREIGN PATENT DOCUMENTS

| JP | 63-288133 | 11/1988 |
| JP | 6-503733 | 4/1994 |
| WO | WO92/03084 | 3/1992 |

* cited by examiner

Primary Examiner—Marvin M. Lateef
Assistant Examiner—Eleni Mantis Mercader
(74) Attorney, Agent, or Firm—Fitzpatrick, Cella, Harper & Scinto

(57) ABSTRACT

Disclosed is a blood vessel detecting apparatus which accurately detects a blood vessel using an image pickup element having a plurality of pixels to pick up an image of a blood vessel, a detector for detecting a pixel output estimated as a blood vessel on the basis of pixel the output from the image pickup elements, and a determination unit for, when the detector detects pixel outputs that are likely to be a plurality of blood vessels, determining a correct number of blood vessels using the pixel output or an area image pickup element.

21 Claims, 21 Drawing Sheets

FIG. 8G

TRACKING REFERENCE POSITION

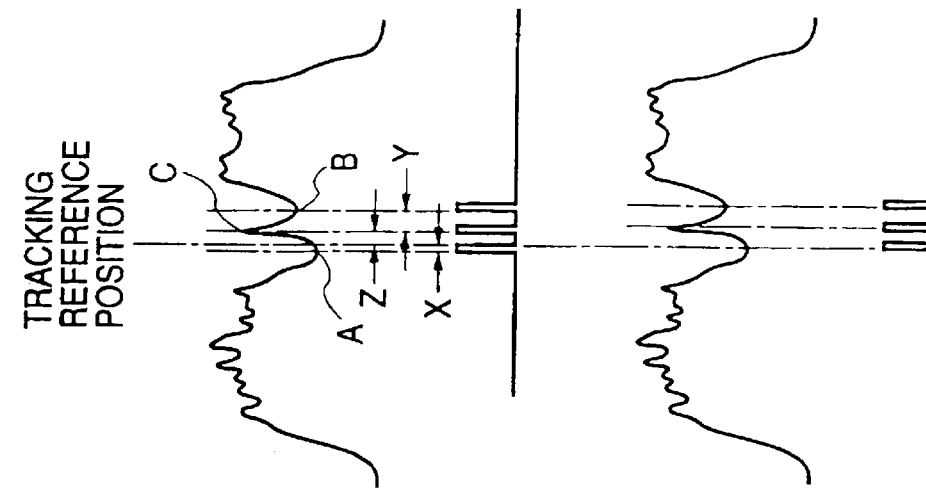
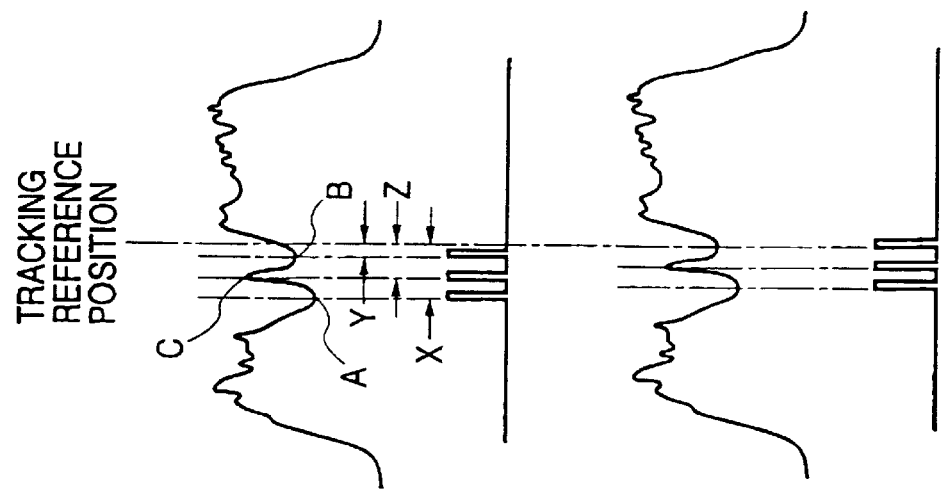
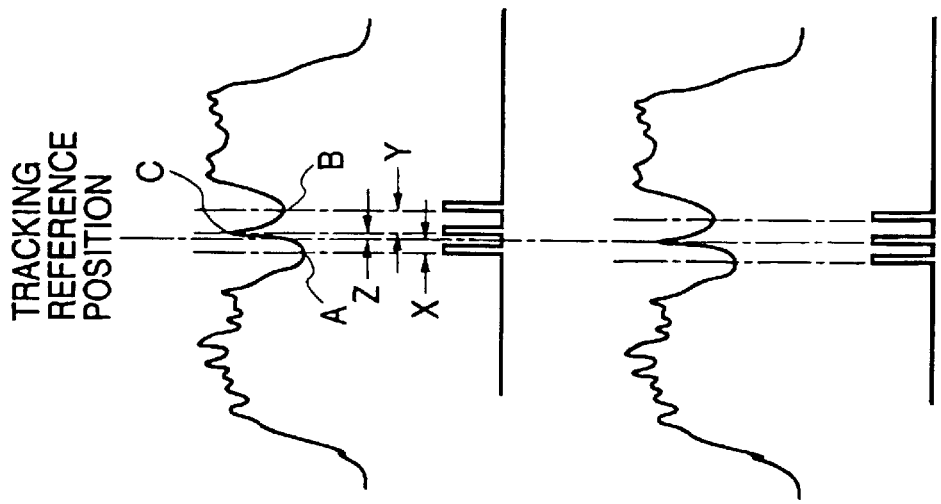

FIG. 11A
FIG. 11B
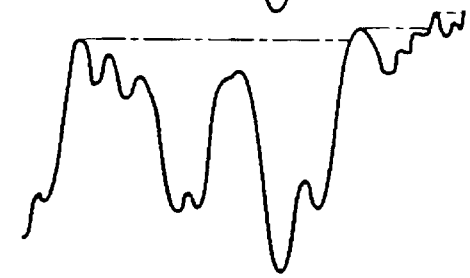
FIG. 11C
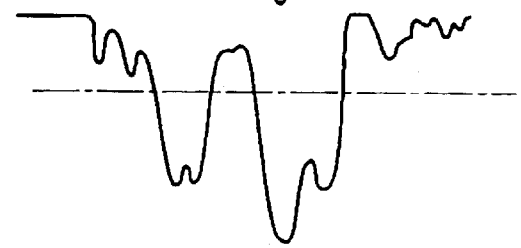
FIG. 11D
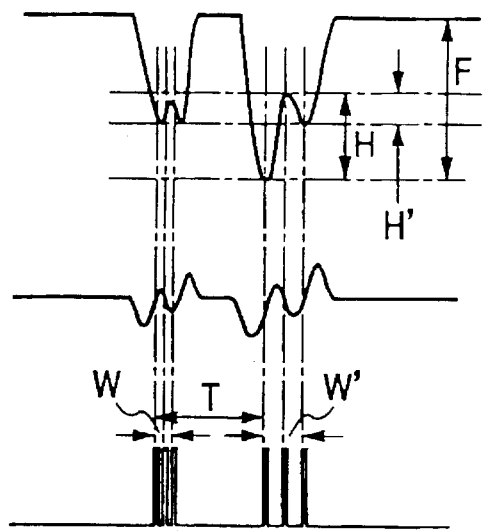
FIG. 11E
FIG. 11F
FIG. 11G
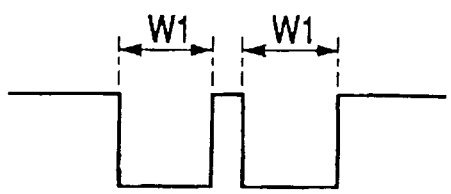
FIG. 11H

BLOOD VESSEL DETECTING APPARATUS

BACKGROUND OF THE INVENTION

1. Field of the Invention

The present invention relates to a fundus examination apparatus for examining blood vessels on patient's fundus in ophthalmic hospitals or the like.

2. Related Background Art

Conventionally, a fundus hemodromometer or blood flow meter irradiates a blood vessel on the fundus of an eye to be examined with a laser beam having a wavelength $\lambda$, receives scattered reflected light by a photodetector, detects an interference signal between a Doppler shift component as the scattered reflected light from the bloodstream in the blood vessel and scattered reflected light from the blood vessel and analyzes the frequency of the signal to obtain the blood flow velocity.

The blood flow velocity can be obtained from a maximum velocity Vmax given by:

$$V_{max} = \{\lambda/(n \cdot \alpha)\} \cdot ||\Delta fmax1| - |\Delta fmax2||/\cos\beta \quad (1)$$

where $\Delta fmax1$ and $\Delta fmax2$ are the maximum shifts of frequencies calculated from light-receiving signals obtained by two light-receiving devices, n is the refractive index at the measurement portion, $\alpha$ is the angle between the two light-receiving axes in an eye, and $\beta$ is the angle between the plane formed by the two light-receiving axes in the eye and the velocity vector of blood flow.

When measurement is done from two directions, contributions of measurement light in the incidence directions are canceled out, and the blood flow velocity at an arbitrary portion on the fundus can be measured. In addition, when the line of intersection between the plane formed by two light-receiving axes and the fundus is made to coincide with the angle $\beta$ the plane makes with the velocity vector of the bloodstream, the actual maximum blood flow velocity can be measured because $\beta = 0°$.

In such a fundus hemodromometer for measuring the blood vessel shape or blood flow velocity at a specific portion of a fundus blood vessel using a laser beam, the measurement portion must be accurately irradiated with the measurement light beam during the measurement processing time. However, actually, it is difficult to continuously accurately irradiate the measurement portion with the measurement light beam because of involuntary eye movement of the eye to be examined. Apparatuses having a tracking means for detecting a blood vessel position and moving the measurement light beam irradiation point on the measurement portion in real time in correspondence with involuntary eye movement are disclosed in, e.g., Japanese Laid-Open Patent Application No. 63-288133 and PCT Laid-Open No. 6-503733.

In these ophthalmic apparatuses, a linear CCD is used as a light-receiving means for receiving a tracking light beam reflected by the fundus to process the waveform of a blood vessel image signal. Tracking is performed by calculating the displacement amount between the tracking reference position and blood vessel image position signal. The fundus is irradiated with tracking light and measurement light through mirrors set at the pupil conjugate positions. When a plurality of blood vessel image position signals are present, tracking may be controlled on the basis of a blood vessel position signal closest to the tracking reference position.

In the above prior arts, however, when a thick blood vessel with high contrast is selected as an object to be measured, regular reflected light from the blood vessel wall is observed at the center of the blood vessel, and an image signal is observed as if there were two blood vessels. In this case, two or more blood vessel position signals are present. For this reason, when tracking is controlled on the basis of the blood vessel position signal closest to the tracking reference position, the blood vessel position closest to the tracking reference position changes due to involuntary eye movement of the eye to be examined, and tracking becomes unstable.

SUMMARY OF THE INVENTION

It is an object of the present invention to solve the above problem and provide an apparatus capable of accurately detecting a blood vessel.

It is another object of the present invention to provide a fundus examination apparatus for easily and accurately measuring fundus blood vessel information by accurate tracking.

A blood vessel detecting apparatus of the present invention is characterized by comprising:

image pickup means for picking up an image of a blood vessel;

detection means for detecting a portion estimated as a blood vessel on the basis of an output from said image pickup means; and determination means for, when said detection means detects a plurality of portions that are likely to be blood vessels, determining the correct number of blood vessels on the basis of the output.

Especially, when the detection means detects a plurality of portions that are likely to be blood vessels, and the portions that are likely to be blood vessels are present within a predetermined width, the determination means determines that the number of blood vessels is one, and when the portions that are likely to be blood vessels are separated by a distance greater than the predetermined width, the determination means determines that the number of blood vessels is two.

There is also provided a blood vessel detecting apparatus comprising:

an area sensor for picking up an image of a blood vessel; and a processing circuit for executing a signal processing operation to extract a feature point of the blood vessel on the basis of an image output from the area sensor concerning a direction perpendicular to a flowing direction of blood in the blood vessel, formed on the area sensor.

Other objects, features, and advantages of the present invention will be apparent from the following description taken in conjunction with the accompanying drawings.

BRIEF DESCRIPTION OF THE DRAWINGS

FIGS. 8A, 8B, 8C, 8D, 8E, 8F, 8G and 8H are graphs showing the tracking signals of two blood vessels;

FIGS. 10A, 10B and 10C are graphs showing the deviation amount from the tracking reference position for a thick blood vessel;

FIGS. 11A, 11B, 11C, 11D, 11E, 11F, 11G and 11H are graphs showing the deviation amount from the tracking reference position when two blood vessels are adjacent to each other;

DETAILED DESCRIPTION OF THE PREFERRED EMBODIMENTS

Embodiments of the present invention will be described in detail with reference to the accompanying drawings.

Figure 1:
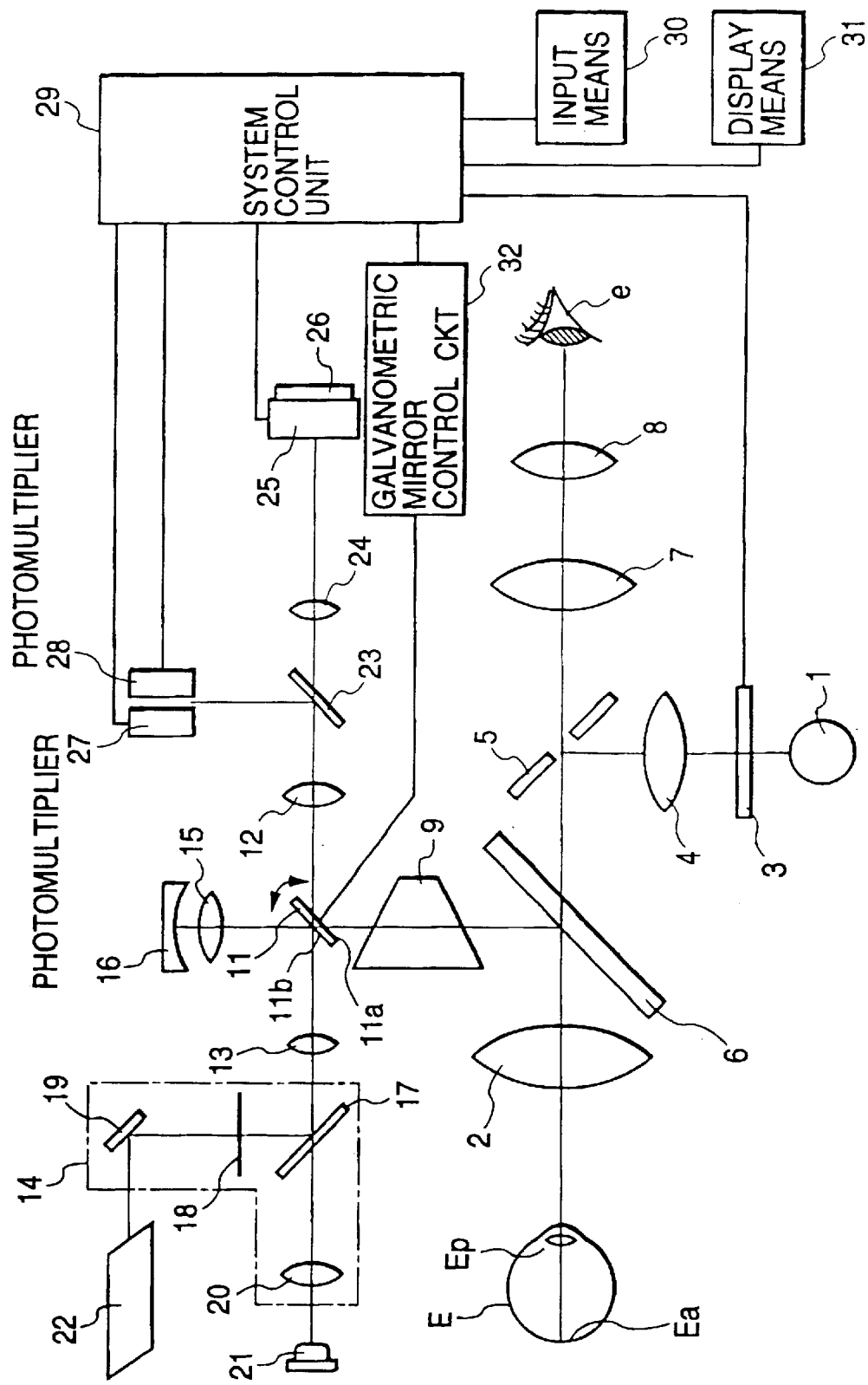
FIG. 1 is a view showing the arrangement of an embodiment.

FIG. 1 is a view showing the arrangement of a fundus hemodromometer according to an embodiment. On the illumination optical path from an observation light source 1 formed from, e.g., a tungsten lamp for emitting white light to an eye E to be examined, a transmission liquid crystal plate 3 as a fixation index display element, which is at a position substantially optically conjugate to the fundus of the eye E to be examined and movable along the optical path, a relay lens 4, a mirror 5 with a hole therein, and a bandpass mirror 6 that transmits light in the yellow wavelength range and reflects most other light components, are sequentially inserted. A fundus observation optical system is formed behind the mirror 5 with the hole. An imaging lens 7 movable along the optical path and an ocular 8 are arranged on the optical path leading to an eye e of an ophthalmic technician.

On the optical path in the reflecting direction of the bandpass mirror 6, an image rotator 9 and galvanometric mirror 11 having a rotating shaft vertical to the page and polished surfaces are arranged. A relay lens 12 movable along the optical path is arranged in the reflecting direction of a lower reflecting surface 11a of the galvanometric mirror 11. A lens 13 having a front focal plane conjugate to the pupil of the eye E to be examined and focus unit 14 movable along the optical path are arranged in the reflecting direction of an upper reflecting surface 11b. The galvanometric mirror 11 has a notch at the lower portion of the rotating shaft and is arranged on the front focal plane of the lens 13. A lens 15 and concave mirror 16 are arranged behind the galvanometric mirror 11 to construct a relay optical system for guiding a light beam which has passed through the notch portion without being reflected by the lower reflecting surface 11a of the galvanometric mirror 11 to the upper reflecting surface 11b of the galvanometric mirror 11.

In the focus unit 14, a dichroic mirror 17 is disposed on the same optical path as that of the lens 13, and a mask plate 18 having a rectangular stop and mirror 19 are inserted on the optical path in the reflecting direction of the dichroic mirror 17. A lens 20 is disposed on the optical path in the transmitting direction of the dichroic mirror 17. The focus unit 14 can be integrally moved. A measurement light source 21, such as a laser diode for emitting collimated coherent red light, is set on the optical path in the incidence direction of the lens 20. A high-luminance tracking light source 22 for emitting, e.g., a green helium neon laser beam, different from light from the remaining light sources, is placed on the optical path in the incidence direction of the mirror 19.

The relay lens 12 movable along the optical path, dichroic mirror 23, an enlargement lens 24, an image intensifier 25, and a linear CCD 26 are sequentially arranged on the optical path in the reflecting direction of the lower reflecting surface 11a of the galvanometric mirror 11 to construct a blood vessel detection system. Photomultipliers 27 and 28 are disposed in the reflecting direction of the dichromic mirror 23 to construct a measurement light-receiving optical system for measuring blood flow velocity. For the illustrative convenience, all optical paths are illustrated on the same plane. Actually, the reflecting direction of the dichroic mirror 23 is perpendicular to the page of FIG. 1.

A system control unit 29 controls the entire apparatus. The output from the image intensifier 25, the linear CCD 26, photomultipliers 27 and 28, and input means 30, operated by an ophthalmic technician, are connected to the system control unit 29. The output from the system control unit 29 are connected to a display means 31 for displaying a measurement result and a galvanometric mirror control circuit 32 for controlling the galvanometric mirror 11.

When a focusing knob (not shown) is operated, the transmission liquid crystal plate 3, the imaging lens 7, the relay lens 12, and the focus unit 14 synchronously move in the direction of the optical axis such that the light-receiving surfaces of the transmission liquid crystal plate 3, the eye E of ophthalmic technician, the mask plate 18, and the image intensifier 25 are always optically conjugate to a fundus Ea of the eye E to be examined.

Figure 2:
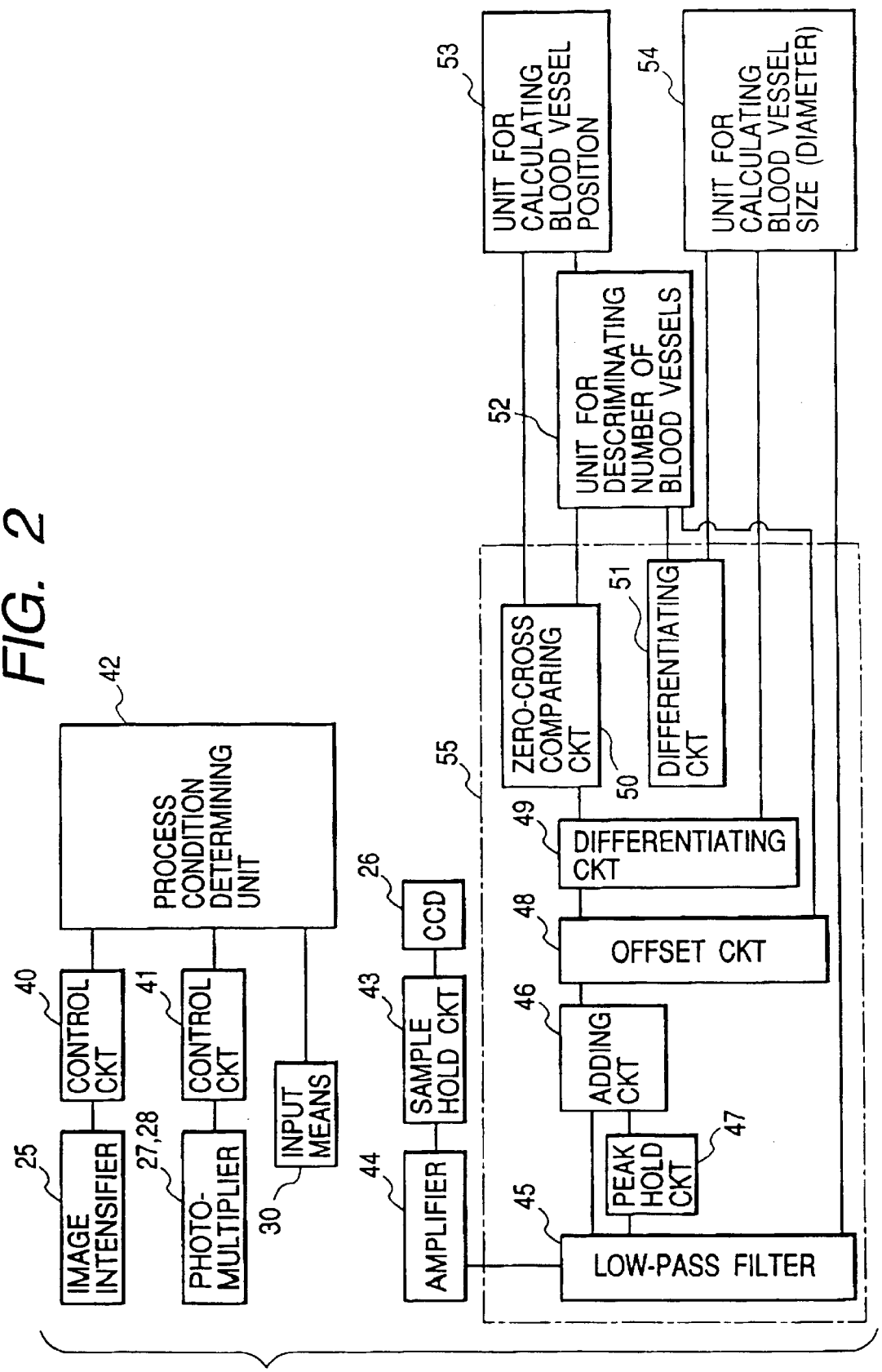
FIG. 2 is a block diagram showing a system control unit.

FIG. 2 is a block diagram of the system control unit 29. The output from the image intensifier 25 and photomultipliers 27 and 28 are connected to a process condition determining unit 42 through control circuits 40 and 41, respectively. The output from the input means 30 is also connected to the process condition determining unit 42.

The output from the linear CCD 26 is connected to a low-pass filter 45 through a sample hold circuit 43 and amplifier 44. An output from the low-pass filter 45 is connected to an adding circuit 46 together with another output through a peak hold circuit 47. The output from the adding circuit 46 is sequentially connected to an offset circuit 48 for removing an unnecessary signal level and a differentiating circuit 49. Outputs from the differentiating circuit 49 are connected to a zero-cross comparing circuit 50 and a differentiating circuit 51.

Outputs from the zero-cross comparing circuit 50 are connected to a unit 52 for discriminating the number of blood vessels and a unit 53 for calculating the blood vessel position. An output from the unit 52 for discriminating the number of blood vessels is connected to the unit 53 for the calculating blood vessel position. The output from the unit 53 for calculating blood vessel position, which constructs a tracking control system, is connected to the galvanometric mirror control circuit 32. Outputs from the offset circuit 48 and differentiating circuit 51 are connected to the unit 52. The other output from the differentiating circuit 51 is connected to a unit 54 for calculating blood vessel size (diameter). Other outputs from the differentiating circuit 49 and unit 52 are also connected to the unit 54. The low-pass filter 45, the adding circuit 46, the peak hold circuit 47, the offset circuit 48, the differentiating circuits 49 and 51, and the zero-cross comparing circuit 50 construct a singular point extraction unit 55.

In this arrangement, white light emitted from the observation light source 1 illuminates the transmission liquid crystal plate 3 from the rear side and is reflected by the mirror 5 with a hole through the relay lens 4. Only light with a wavelength in the yellow range passes through the bandpass mirror 6 and objective lens 2. The image of light is temporarily formed on a pupil Ep of the eye E to be examined as a fundus illumination light image and then almost uniformly illuminates the fundus Ea. A fixation index (not shown) is displayed on the transmission liquid crystal plate 3. This fixation index is projected onto the fundus Ea of the eye E to be examined by illumination light and is presented on the eye E to be examined as an indicator image.

The light reflected by the fundus Ea returns along the same optical path and is extracted from the pupil Ep as a fundus observation light beam. The light passes through the opening at the center of the mirror 5 with the hole and the imaging lens 7, so a fundus image Ea' can be observed by the eye e of ophthalmic technician through the ocular 8.

Measurement light from the measurement light source 21 is collimated and transmitted through the lens 20 and dichroic mirror 17. Tracking light from the tracking light source 22 is reflected by the mirror 19, shaped to a desired shape by the mask plate 18, reflected by the dichroic mirror 17, and superposed on the measurement light. At this time, a spot image of measurement light is formed at a position conjugate to the center of opening of the mask plate 18 through the lens 20.

The measurement light and tracking light pass through the lens 13, are reflected by the upper reflecting surface 11b of the galvanometric mirror 11, pass through the lens 15, are reflected by the concave mirror 16, pass through the lens 15 again, and return to the galvanometric mirror 11. The galvanometric mirror 11 is at a position conjugate to the pupil of the eye E to be examined. The concave mirror 16 and lens 15 are concentrically set on the optical axis to function in combination as a relay system for forming a $-1\times$ image on the galvanometric mirror 11. For this reason, the light beams are returned to the notch portion of the galvanometric mirror 11. The light beams propagate to the image rotator 9 without being reflected by the galvanometric mirror 11. The light beams that have passed through the image rotator 9 are deflected by the bandpass mirror 6 toward the objective lens 2 to irradiate the fundus Ea of the eye E to be examined through the objective lens 2.

When the measurement light and tracking light are reflected by the upper reflecting surface 11b of the galvanometric mirror 11, the light beams are incident on the galvanometric mirror 11 while being decentered from the optical axis of the objective lens 2. The light beams form spot images on the pupil Ep, and the spot light irradiates the fundus Ea.

Scattered reflected light from the fundus Ea due to the measurement light and tracking light is condensed by the objective lens 2 again. Most light components are reflected by the bandpass mirror 6, pass through the image rotator 9, are reflected by the lower reflecting surface 11a of the galvanometric mirror 11, and pass through the relay lens 12, so the measurement light and tracking light are split by the dichroic mirror 23.

The tracking light passes through the dichroic mirror 23. The image of the tracking light is formed on the photoelectric surface of the image intensifier 25 through the enlargement lens 24 as a blood vessel image Ev' larger than the fundus image Ea' by the fundus observation optical system, amplified, and picked up by the linear CCD 26. Date representing the moving amount of the blood vessel image Ev' is generated by the system control unit 29 on the basis of the blood vessel image Ev' picked up by the linear CCD 26. The blood vessel image Ev' and moving amount are output to the galvanometric mirror control circuit 32. The galvanometric mirror control circuit 32 drives the galvanometric mirror 11 to compensate for the moving amount, thereby tracking the blood vessel at the measurement portion.

On the other hand, the measurement light is reflected by the dichroic mirror 23 and received by the photomultipliers 27 and 28. The output from the photomultipliers 27 and 28 are input to the system control unit 29. The frequencies of the light-receiving signals are analyzed to obtain the blood flow velocity on the fundus Ea, as in the prior art.

The scattered reflected light from the fundus Ea due to the measurement light and tracking light is condensed by the objective lens 2. Some light components that have passed through the bandpass mirror 6 reach the eye e of an ophthalmic technician along the same optical path as that of the scattered reflected light from the fundus Ea by the observation light source 1, so the ophthalmic technician can observe a measurement light image and tracking indicator image A together with the fundus image Ea'.

To examine a fundus blood vessel, first, the ophthalmologist or ophthalmic technician operates an operation handle (not shown) to perform positioning such that the optical axis of the eye E to be examined matches that of the objective lens 2. Next, a focus knob (not shown) is operated while observing the fundus image Ea' to focus on the fundus Ea of the eye E to be examined. In an in-focus state, the fixation index on the transmission liquid crystal plate 3 and the fundus Ea in an optically conjugate state are presented on the eye E to be examined. When the person under examination looks at the fixation index, the ophthalmic technician can observe the fundus image Ea' of the eye E to be examined.

The ophthalmic technician operates the input means 30 to move the fixation index such that the target measurement portion is set substantially near the center of the observation field, thereby guiding the eye E to be examined.

Next, the input means 30 is operated to irradiate the fundus Ea with tracking light. A rotator operation knob (not shown) is operated to make the tracking indicator image A perpendicular to the blood vessel to be measured. The angle of the galvanometric mirror 11 is controlled to irradiate the blood vessel to be measured with measurement light.

Figure 3:
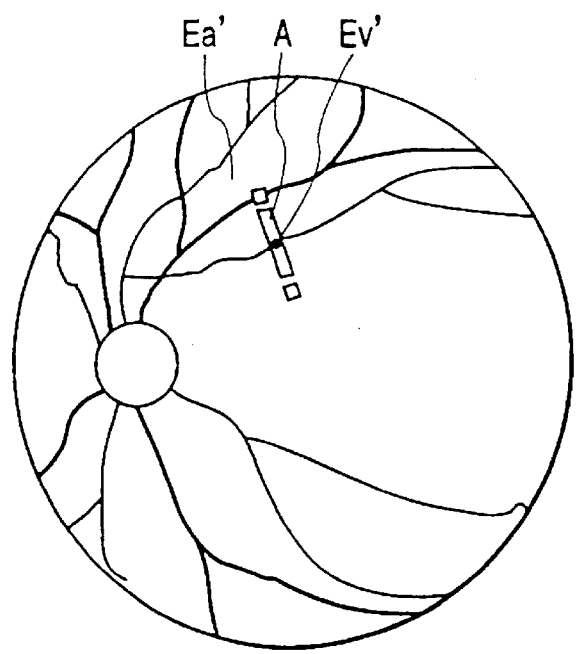
FIG. 3 is an explanatory view of an observed fundus image.
Figure 4:
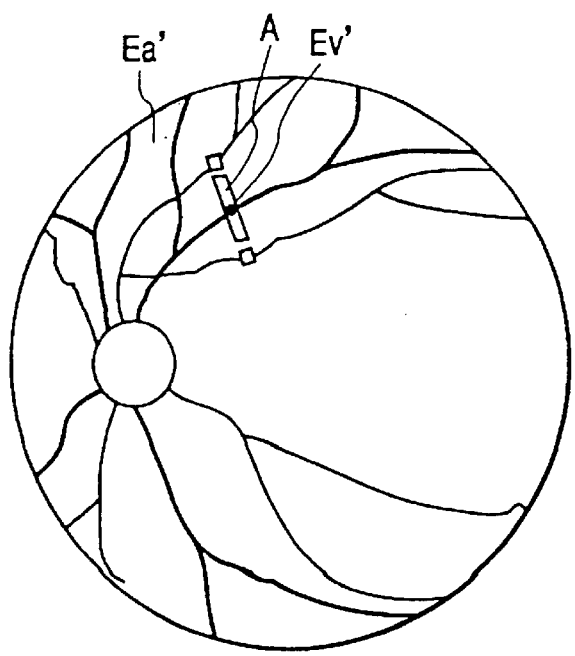
FIG. 4 is an explanatory view of an observed fundus image.
Figure 5:
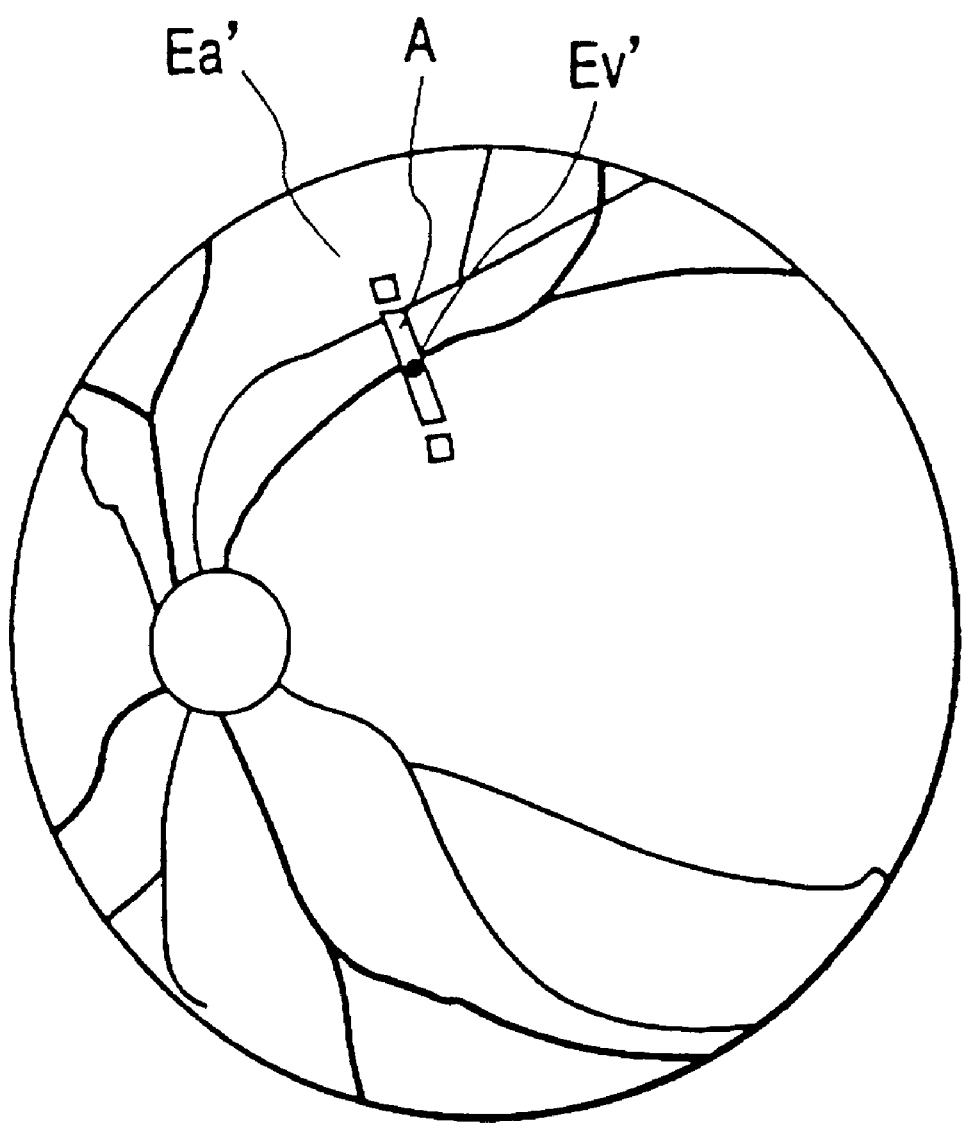
FIG. 5 is an explanatory view of an observed fundus image.

FIG. 3 shows the fundus image Ea' observed at this time. FIG. 3 shows a case wherein a thin blood vessel is selected as an object to be measured, and FIGS. 4 and 5 show cases wherein thick blood vessels are selected. In FIG. 4, one thick blood vessel is irradiated with tracking light. In FIG. 5, two blood vessels are irradiated. The image of a blood vessel Ev irradiated with tracking light is formed on the photoelectric surface of the image intensifier 25 as the blood vessel image Ev', amplified, picked up by the linear CCD 26, and output as a blood vessel image signal.

Figure 6A:
FIGS. 6A, 6B, 6C, 6D, 6E and 6F are graphs showing the tracking signal of a thin blood vessel.
Figure 6B:

FIGS. 6A to 6F show the flow of a tracking signal when a thin blood vessel in which no regular reflection from the blood vessel wall is present at the center is selected as an object to be measured. The ophthalmic technician decides the measurement portion and then operates the input means 30 again to input the start of tracking. An output signal from the linear CCD 26 is sampled/held by the sample hold circuit 43, input to the amplifier 44, and amplified by an appropriate gain. An output signal waveform shown in FIG. 6A is obtained. This output signal is input to the low-pass filter 45 and subjected to noise removal processing to remove unnecessary high-frequency components, so a waveform shown in FIG. 6B is output.

Peak hold processing is performed by the peak hold circuit 47 to extract only the blood vessel image. Output signals from the low-pass filter 45 and peak hold circuit 47 are added by the adding circuit 46 to obtain a signal waveform shown in FIG. 6C. An output signal from the adding circuit 46 is input to the offset circuit 48 to calculate the signal amplitude first. On the basis of the amplitude information of this signal, a level at which unnecessary signal components are removed is determined. The background portion unnecessary for singular point (feature point) extraction of the blood vessel portion is saturated using the offset circuit 48 and removed to obtain a signal waveform shown in FIG. 6D.

Figure 6C:
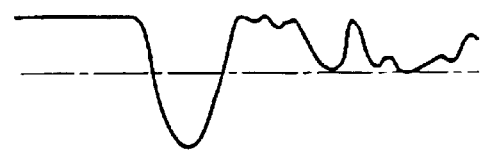
Figure 6D:
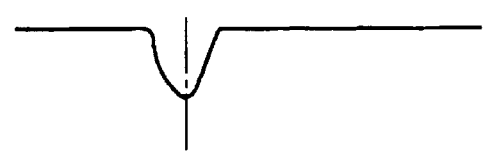
Figure 6E:

In this embodiment, the offset amount is determined to be about ⅓ the amplitude indicated by the broken line in FIG. 6C. The unnecessary background portion is saturated by multiplying the waveform by the offset and removed. The offset level is fixed at ⅓ the amplitude. However, the offset level may be changed in accordance with the signal amplitude or the like. An output signal from the offset circuit 48 is differentiated by the differentiating circuit 49. A waveform shown in FIG. 6E is output and input to the zero-cross comparing circuit 50. After a zero-cross point is extracted, this signal is input to the unit 53 for calculating the blood vessel position and is used as a blood vessel position signal.

Figure 6F:

An output signal from the differentiating circuit 49 is input to the differentiating circuit 51. An output signal from the differentiating circuit 51 is input to the unit 52 for discriminating the number of blood vessels. It is determined by sign determination whether the zero-cross point extracted by the zero-cross comparing circuit 50 is calculated from the maximal or minimal point of the blood vessel image. In this case, since there is only one zero-cross point, the unit 52 determines that the number of blood vessels is one. This result is output to the unit 53 for calculating blood vessel position, and a blood vessel position signal as shown in FIG. 6F is output from the unit 53.

FIGS. 7A to 7H show the flow of tracking signal processing when a thick blood vessel as shown in FIG. 4 is irradiated with a tracking beam. FIGS. 8A to 8H show the flow of tracking signal processing when two blood vessels as shown in FIG. 5 are irradiated with a tracking beam.

Figure 9A:
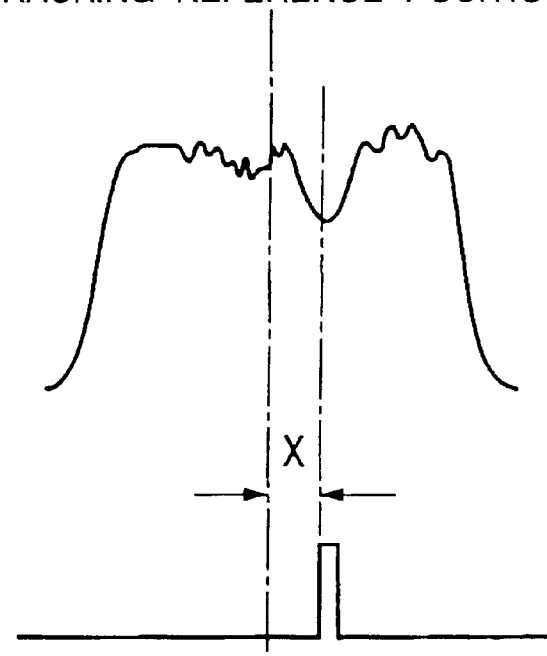
FIGS. 9A and 9B are graphs showing the deviation amount from the tracking reference position for a thin blood vessel.
Figure 9B:
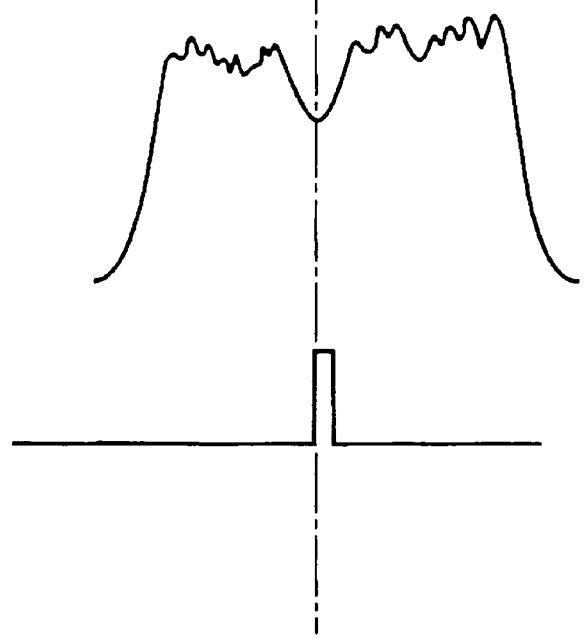

As shown in FIG. 3, when a thin blood vessel is selected as an object to be measured, the unit 53 for calculating blood vessel position calculates a deviation amount X of the blood vessel position signal closest to the tracking reference position, as shown in FIG. 9A. The galvanometric mirror 11 is driven and controlled by the galvanometric-mirror control circuit 32 on the basis of this deviation amount X such that the image reception position of the blood vessel image Ev' on the linear CCD 26 matches the tracking reference position, as shown in FIG. 9B. The spot measurement light beam is superposed at the central position corresponding to the linear reference position of the tracking light to irradiate the fundus Ea. Hence, the measured blood vessel Ev can be accurately detected by the tracking system.

When a thick blood vessel with high contrast as shown in FIG. 4 is selected as an object to be measured, regular reflection from the blood vessel wall is observed at the center of the blood vessel, and an image signal may be observed as if two blood vessels were present. In this case, when a zero-cross point is used as a blood vessel position signal, three points A, B, and C are extracted, as shown in FIGS. 10A to 10C. FIGS. 10A, 10B, and 10C show fundus image signals and blood vessel position signals when the fundus image changes due to eye movement such as involuntary eye movement. The unit 53 for calculating blood vessel position calculates the deviation of a blood vessel position signal closest to the tracking reference position to perform tracking. In FIG. 10A, deviations X, Y, and Z of the three points A, B, and C have a relation Z<Y<X. For this reason, control is performed to set the point C at the tracking reference position. Similarly, in FIG. 10B, since Y<Z<X, the point B is tracked. In FIG. 10C, since X<Z<Y, the point A is tracked. As a result, when eye movement such as involuntary eye movement is observed, tracking becomes unstable.

Figure 7A:
FIGS. 7A, 7B, 7C, 7D, 7E, 7F, 7G and 7H are graphs showing the tracking signal of a thick blood vessel.
Figure 7B:
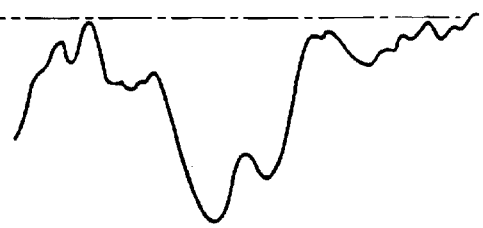
Figure 7C:
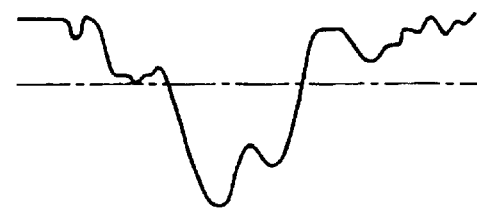
Figure 7D:
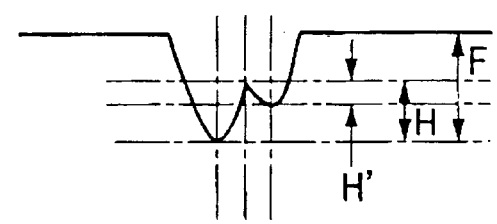
Figure 7E:
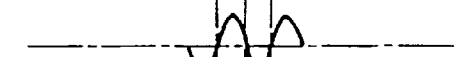
Figure 7F:
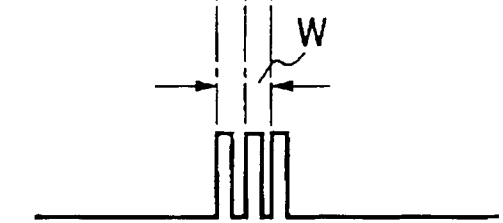
Figure 7G:
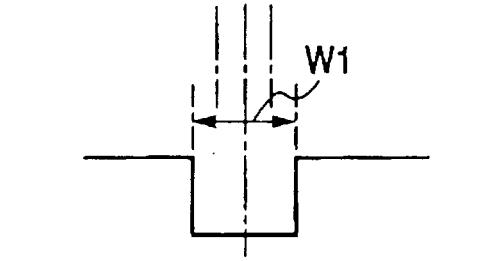
Figure 7H:

When a plurality of blood vessel position signals are present, the output signal from the differentiating circuit 49 is further differentiated by the differentiating circuit 51. From the sign of an output signal from the differentiating circuit 51 in synchronism with a zero-cross point output from the zero-cross comparing circuit 50, the unit 52 for discriminating the number of blood vessels determines whether the zero-cross point is generated from the maximal or minimal point of the blood vessel image. Next, the unit 52 extracts three zero-cross points at the minimal, maximal, and minimal points as one group, measures the distance between the tracking signals at the minimal points, and compares it with a predetermined width W1. As shown in FIG. 7E, when a distance W between the zero-cross points at the minimal points is equal to or smaller than the width W1, the unit 52 recognizes that the number of blood vessels is one and outputs the result to the unit 53 for calculating blood vessel position.

The unit 52 for discriminating the number of blood vessels also calculates level differences H and H' between the two minimal points and maximal point of the signal waveform input from the offset circuit 48 and compares a larger one of the level differences H and H' with a maximum amplitude F. In this embodiment, when H<F*0.5, the unit 52 recognizes that the number of blood vessels is one. On the basis of two parameters, i.e., the distance W between the zero-cross points at the minimal points and the level difference H between the minimal point and maximal point, the unit 52 determines that the number of blood vessels is one, and outputs the information of the number of blood vessels to the unit 53 for calculating blood vessel position.

Figure 8A:
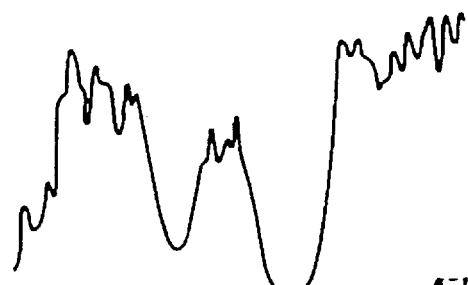
Figure 8B:
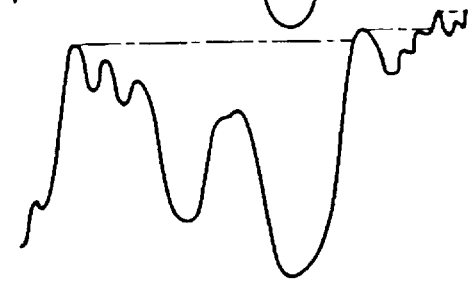
Figure 8C:
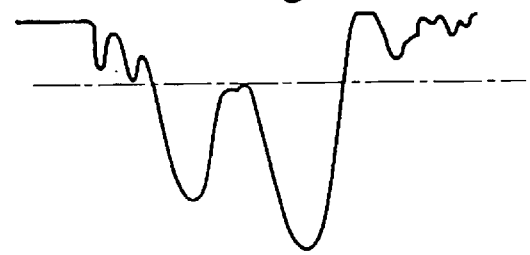
Figure 8D:
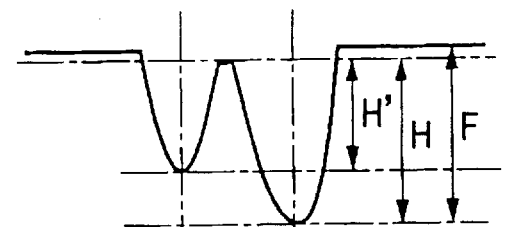
Figure 8E:
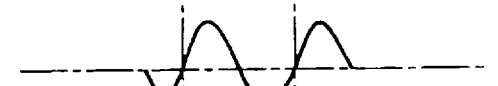
Figure 8F:
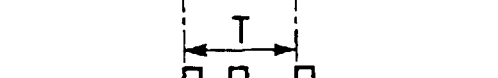

As shown in FIG. 8E, when a distance T between the zero-cross points at the minimal points is equal to or larger than the width W1, the unit 52 for discriminating the number of blood vessels recognizes that the number of blood vessels is two. Next, the unit 52 calculates the level differences H and H' between the two minimal points and maximal point of the signal waveform input from the offset circuit 48 and compares a larger one of the level differences H and H' with the maximum amplitude F, as shown in FIG. 8D. In this embodiment, when H<F*0.5, the unit 52 recognizes that the number of blood vessels is one. For this reason, the unit 52 determines that the number of blood vessels is two.

Figure 8H:
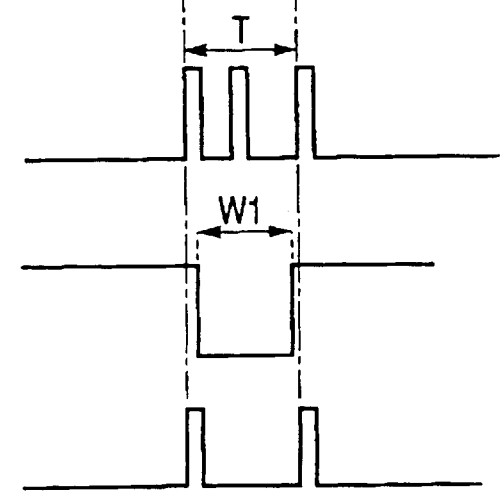

On the basis of two parameters, i.e., the distance W between the zero-cross points at the minimal points and the level difference H between the minimal point and maximal point, the unit 52 for discriminating the number of blood vessels determines that the number of blood vessels is two, and outputs the information of the number of blood vessels to the unit 53 for calculating blood vessel position. The unit 53 uses only the minimal points as blood vessel position signals and outputs a blood vessel position signal as shown in FIG. 8H. When tracking is performed on the basis of this blood vessel position signal, stable tracking performance can be obtained.

FIGS. 11A to 11H show a case wherein two blood vessels are adjacent to each other, and regular reflection from the blood vessel wall is observed at each blood vessel center, so an image signal is observed as if there were four blood vessels. In this case as well, the unit 52 for discriminating the number of blood vessels determines, on the basis of the sign of an output signal from the differentiating circuit 51 in synchronism with the zero-cross point of the output from the zero-cross comparing circuit 50, whether the zero-cross point is generated from the maximal or minimal point of the blood vessel image waveform. The unit 52 extracts three blood vessel position signals at the minimal, maximal, and minimal points as one group and measures the distance T between two groups. The distance T is compared with the predetermined width W1. Since T>W1, the unit 52 recognizes that the number of blood vessels is two or more. As shown in FIG. 11D, since the level differences between the two minimal points and maximal point equal the maximum amplitude F, it is determined that the number of blood vessels is two or more. Subsequently, the distances W and W' between the zero-cross points at the minimal points of the respective groups are measured and compared with the predetermined width W1. Since W<W1 and W'<W1, it is determined that the number of blood vessels in each group is one.

For the group on the right side in FIG. 11D, the level differences H and H' between the two minimal points and maximal point are calculated and a larger one of the level differences H and H' is compared with the maximum amplitude F. Since H>F*0.5, it is determined that the number of blood vessels is one. The same processing as described above is performed for the group on the left side, and the result is output to the unit 53 for calculating blood vessel position. The unit 52 for discriminating the number of blood vessels performs processing while neglecting the zero-cross points of the minimal points at two ends of each group and regarding the maximal point at the center as the blood vessel center, and outputs a blood vessel position signal as shown in FIG. 11H.

In this embodiment, the predetermined width W1 and the level difference of 0.5 between the two minimal points and maximal point for the amplitude are fixed. However, the value W1 may be input to the input means 30 and manually set in accordance with the blood vessel to be measured by the ophthalmic technician who is observing the fundus image Ea'.

The above description has been made on the basis of an embodiment applied to the blood vessel tracking system of a fundus hemodromometer. Even in blood vessel size (diameter) measurement, the same arrangement and effect as described above can be realized in association with a blood vessel specification. In this case, not the blood vessel position but the blood vessel size (diameter) is calculated as information perpendicular to the blood vessel running direction (i.e. a flowing direction of blood), and the flow of control is as follows.

Output signals from the low-pass filter 45, the differentiating circuit 49, the differentiating circuit 51, and the unit 52 for discriminating the number of blood vessels are input to the unit 54 for calculating blood vessel size (diameter) and are used as original signals for blood vessel size (diameter) calculation, i.e., feature points of the blood vessel image, information for determination of maximal and minimal points of the blood vessel image, and information of the number of blood vessels. The unit 54 for calculating blood vessel size (diameter) calculates the blood vessel size (diameter) on the basis of these pieces of information. The remaining procedures are the same as in calculation of the blood vessel position.

The cutoff frequency of the low-pass filter 45 may be set on the lower side to narrow the passband and remove the regular reflection component from the blood vessel wall by the low-pass filter 45. However, the regular reflection component from the blood vessel wall changes depending on the blood vessel to be measured. When a thin blood vessel is measured, the frequency component of an effective signal of the blood vessel is cut off by the low-pass filter 45. This embodiment can solve this problem, so an accurate blood vessel position signal can be detected.

As described above, in the ophthalmic examination apparatus according to the present invention, at least one of the distance information between a plurality of maximal and minimal points and the amplitude information of the maximal and minimal points, which are detected by a singular point calculation means, is used to calculate blood vessel information. Even when an image signal is observed as if two blood vessels were present due to regular reflection from the blood vessel wall, the case can be clearly discriminated from a case wherein two blood vessels actually adjacent to each other are measured, and a blood vessel image signal of an optimum level can be obtained independently of the contrast. This allows accurate tracking and blood vessel position measurement, so the fundus blood flow velocity and fundus blood flow volume can be accurately and easily obtained.

An apparatus which uses an area image pickup element and can accurately detect a blood vessel within a short processing time will be described next.

The basic arrangement of the blood flow measurement apparatus is the same as that of the above-described embodiment, and this will be described again.

Figure 12:
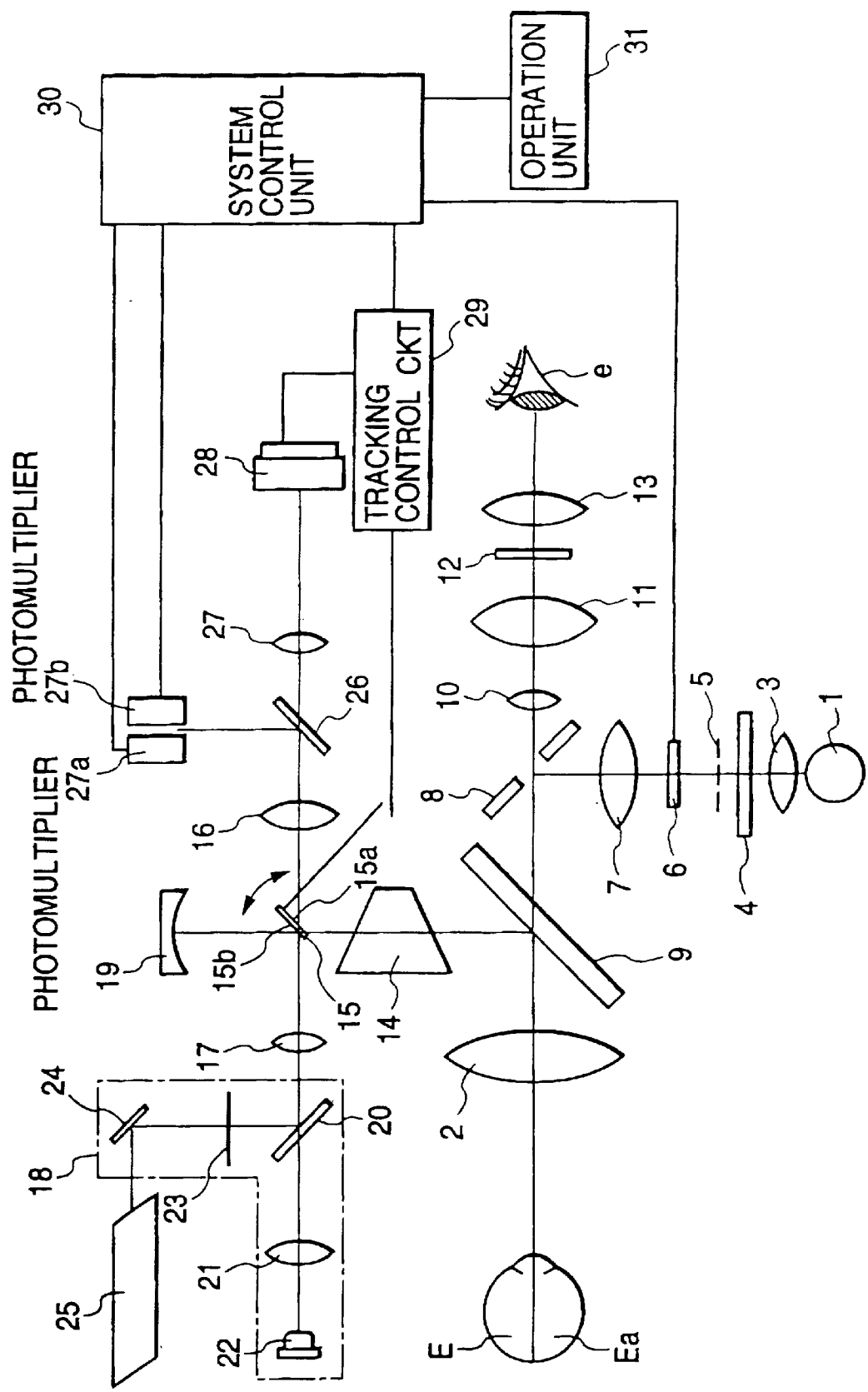
FIG. 12 is a view showing the arrangement of another embodiment.

FIG. 12 shows the arrangement. On the illumination optical path from an observation light source 101 formed from, e.g., a tungsten lamp for emitting white light to an objective lens 102 opposing an eye E to be examined, a condenser lens 103, a bandpass filter 104 for transmitting only, e.g., light in the yellow wavelength range, a ring slit 105 at a position almost conjugate to the pupil of the eye E to be examined, a transmission liquid crystal plate 106 as a fixation index display element movable along the optical path, a relay lens 107, a mirror 108 with a hole and a bandpass mirror 109, which transmits light in the yellow wavelength range and reflects most other light components, are sequentially arranged.

A fundus observation optical system is formed behind the mirror 108 with the hole. A focusing lens 110 movable along the optical path, a relay lens 111, a scale plate 112, and an ocular 113 are sequentially arranged on the optical path leading to an eye e of an ophthalmic technician. On the optical path in the reflecting direction of the bandpass mirror 109, an image rotator 114 and galvanometric mirror 115 having a rotating shaft vertical to the page and polished surfaces are arranged. A focusing lens 116 movable along the optical path is arranged in the reflecting direction of a lower reflecting surface 115a of the galvanometric mirror 115. A lens 117 and a focus unit 118 movable along the optical path are arranged in the reflecting direction of an upper reflecting surface 115b. The front focal plane of the lens 117 is conjugate to the pupil of the eye E to be examined. The galvanometric mirror 115 is arranged on this focal plane. A concave mirror 119 is disposed behind the galvanometric mirror 115 to form a relay optical system for passing a laser beam reflected by the upper reflecting surface 115b of the galvanometric mirror 115 through its notch portion.

In the focus unit 118, a dichroic mirror 120, a condenser lens 121, and a laser diode 122 as a measurement light source are sequentially inserted on the same optical path as that of the lens 117. A mask plate 123 and a mirror 124 are arranged on the optical path in the reflecting direction of the dichroic mirror 120. The focus unit 118 can be integrally moved in a direction indicated by an arrow. A high-luminance tracking light source 125 for emitting, e.g., green light, different from light from the remaining light sources, is placed on the optical path in the incidence direction of the mirror 124.

A dichroic mirror 126, an enlargement lens 127, and a two-dimensional image pickup element (area sensor) 128 with an image intensifier are sequentially arranged behind the focusing lens 116 on the optical path in the reflecting direction of the lower reflecting surface 115a of the galvanometric mirror 115, thereby forming a blood vessel detection system. Photomultipliers 127a and 127b are arranged on the optical path in the reflecting direction of the dichroic mirror 126 to construct a measurement light-receiving optical system. For the illustrative convenience, all optical paths are illustrated on the same plane. Actually, the photomultipliers 127a and 127b are arranged in a direction perpendicular to the page of FIG. 12.

The output from the two-dimensional image pickup element 128 is connected to a tracking control unit 129. An output from the tracking control unit 129 is connected to the galvanometric mirror 115. A system control unit 130 controls the entire apparatus. The system control unit 130 is connected to the transmission liquid crystal plate 106, photomultipliers 127a and 127b, a tracking control unit 129, and an operation unit and controls the operation of the entire apparatus.

White light emitted from the observation light source 101 passes through the condenser lens 103. Only light in the yellow wavelength range passes through the bandpass mirror 104. The light beam transmitted through the ring slit 105 illuminates the transmission liquid crystal plate 106 from the rear side, passes through the relay lens 107, and is reflected by the mirror 108 with the hole. After this, only yellow light is transmitted through the bandpass mirror 109 and the objective lens 102. The image of light is temporarily formed on the pupil of the eye E to be examined as a ring slit image and then almost uniformly illuminates an fundus Ea.

A fixation index is displayed on the transmission liquid crystal plate 106. This fixation index is projected onto the fundus Ea by illumination light and presented on the eye E to be examined as an indicator image. The ring slit 105 splits fundus illumination light and fundus observation light at the front portion of the eye E to be examined. The shape and number of ring slits are not limited as far as a necessary light shielding region can be formed.

The light reflected by the fundus Ea returns along the same optical path and is extracted from the pupil as a fundus observation light beam. The light beam passes through the opening at the center of the mirror 108 with the hole, the focusing lens 110 and the relay lens 111. The image of the light is formed on the scale plate 112 as a fundus image Ea' and observed by the eye e of an ophthalmic technician through the ocular 113. The apparatus is aligned through the ocular 113 while observing the fundus image Ea'.

Measurement light emitted from the laser diode 122 passes through the upper portion of the condenser lens 121 while being decentered and then the dichroic mirror 120. On the other hand, tracking light emitted from the tracking light source 125 is reflected by the mirror 124, shaped into a desired shape by the shaping mask 123, reflected by the dichroic mirror 120, and superposed on the measurement light. At this time, a spot image of measurement light is formed at a position conjugate to the center of the opening of the mask 123 through the condenser lens 121.

The measurement light and tracking light pass through the lens 117, are temporarily reflected by the upper reflecting surface 115b of the galvanometric mirror 115, reflected by the concave mirror 119, and returned to the galvanometric mirror 115 again. The galvanometric mirror 115 is located to be conjugate to the eye E to be examined and has a non-diagonal shape on the pupil of the eye E to be examined.

The concave mirror 119 is concentrically set on the optical axis and has a relay system function of forming 1×images of the upper reflecting surface 115b and lower reflecting surface 115a of the galvanometric mirror 115. Hence, the two light beams reflected by the upper reflecting surface 115b are returned to the notch portion of the galvanometric mirror 115 and propagate to the image rotator 114 without being reflected by the galvanometric mirror 115 again. The light beams pass through the image rotator 114, are deflected by the bandpass mirror 109 toward the objective lens 102, and irradiate the fundus Ea through the objective lens 102.

The tracking light is shaped by the shaping mask 123 to illuminate a rectangular region including a measurement point and covering the blood vessel. The size of the region is preferably about 300 to 500 $\mu$m in the direction the blood vessel runs and about 500 to 1,200 $\mu$m in the direction perpendicular to the blood vessel. The measurement light has a circular spot shape with a diameter of 50 to 120 $\mu$m corresponding to the thickness of the blood vessel to be measured or an elliptical shape long in the blood vessel running direction.

Scattered reflected light from the fundus Ea is condensed by the objective lens 2 again, reflected by the bandpass mirror 109, passes through the image rotator 114, is reflected by the lower reflecting surface 115a of the galvanometric mirror 115, and passes through the focusing lens 116, so the measurement light and tracking light are split by the dichroic mirror 126.

The tracking light is transmitted through the dichroic mirror 126. The image of the tracking light is formed on the two-dimensional image pickup element 128 through the enlargement lens 127 as a blood vessel image Ev larger than the fundus image Ea' by the fundus observation optical system. The image pickup range has almost the same size as that of tracking light irradiation range. The blood vessel image signal is input to the tracking control unit 129 and converted into a blood vessel position signal. The tracking control unit 129 controls the angle of rotation of the galvanometric mirror 115 and tracks the blood vessel using this signal. Since the blood vessel image is picked up through the galvanometric mirror 115 as a light beam deflector, the tracked blood vessel is always in this image pickup range, so the image pickup range can be set within the range of tracking light.

Some components of scattered reflected light from the fundus Ea due to the measurement light and tracking light are transmitted through the bandpass mirror 109 and guided to the fundus observation optical system behind the mirror 108 with hole. The image of tracking light is formed on the scale plate 112 as a rod-shaped indicator. The image of measurement light is formed at the central portion of this indicator as a spot image. These images are observed through the ocular 113 together with the fundus image Ea' and indicator image F. At this time, the spot image of the measurement beam is superposed at the center of the indicator and observed. The indicator can be linearly moved on the fundus Ea by operating an operation unit 131 to rotate the galvanometric mirror 115 through the tracking control unit 129.

Before measurement, the ophthalmic technician focuses on the fundus image Ea'. When the focus knob of the operation unit 131 is adjusted, the transmission liquid crystal plate 106, focusing lenses 110 and 116, and focus unit 118 are synchronously moved along the optical path by a driving means (not shown). In an in-focus state of the fundus image Ea', the transmission liquid crystal plate 106, the scale plate 112, and the two-dimensional image pickup element 128 are simultaneously conjugate to the fundus Ea.

In actual examination, after the fundus image Ea' is set in an in-focus state, the ophthalmic technician guides the line of sight of the eye E to be examined to deflect the observation region and operates the operation unit 131 to move the blood vessel Ev to be measured to an appropriated position. The system control unit 130 controls the transmission liquid crystal plate 106 to move the indicator image F. The image rotator 114 is rotated to set the line connecting the centers of the photomultipliers 127a and 127b parallel to the running direction of the blood vessel Ev to be measured. At this time, when the galvanometric mirror 115 is rotated, the vertical direction of the pixel array of the two-dimensional image pickup element 128 and the direction of moving measurement beam are simultaneously adjusted to be perpendicular to a blood vessel Ea perpendicular to the blood vessel Ev. With this operation an orthogonal coordinate system having axes substantially matching the blood vessel running directions is defined for the image signal to be picked up. In this embodiment, this signal processing is called the first step.

After tracking is started, the ophthalmic technician confirms it, and depresses the measurement switch on the operation unit 131 to start measurement. During this measurement, the measurement beam is held on the blood vessel Ea by the function of the tracking control unit 129. The scattered reflected light of the measurement light is reflected by the dichroic mirror 126 and received by the photomultipliers 127a and 127b. The output from the photomultipliers 127a and 127b are input to the system control unit 130. The frequencies of the light-receiving signals are analyzed to obtain the blood flow velocity on the fundus Ea.

Figure 13:
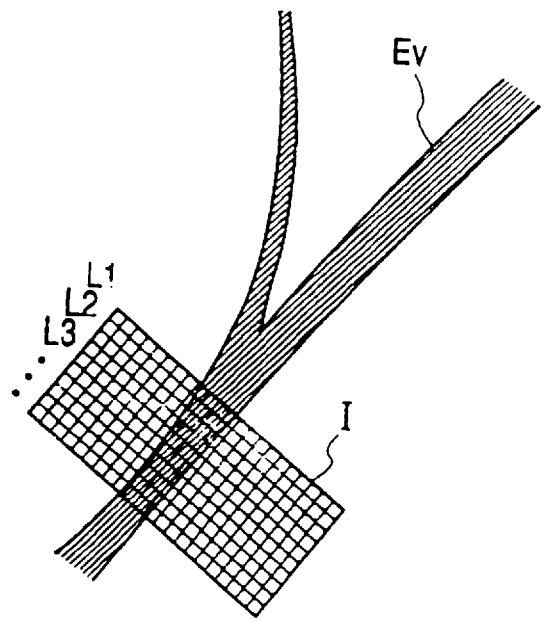
FIG. 13 is an explanatory view of the positional relationship between an image pickup element and a blood vessel to be picked up.

Signal processing by the tracking control unit 129 corresponds to the second step of this embodiment. This processing is performed by a high-speed calculation circuit such as a DSP to shorten the processing time. In FIG. 13, I represents the image pickup range of the two-dimensional image pickup element 128. Electronic scanning is performed in units of lines L1, L2, L3, . . . to output a two-dimensional image signal of the blood vessel Ea. In this embodiment, the scanning direction is already adjusted to be perpendicular to the running direction of the blood vessel Ea in measurement, and the subsequent processing can be relatively simple. For this reason, the time required for signal processing is shortened, and the tracking response speed can be increased.

Figure 14:
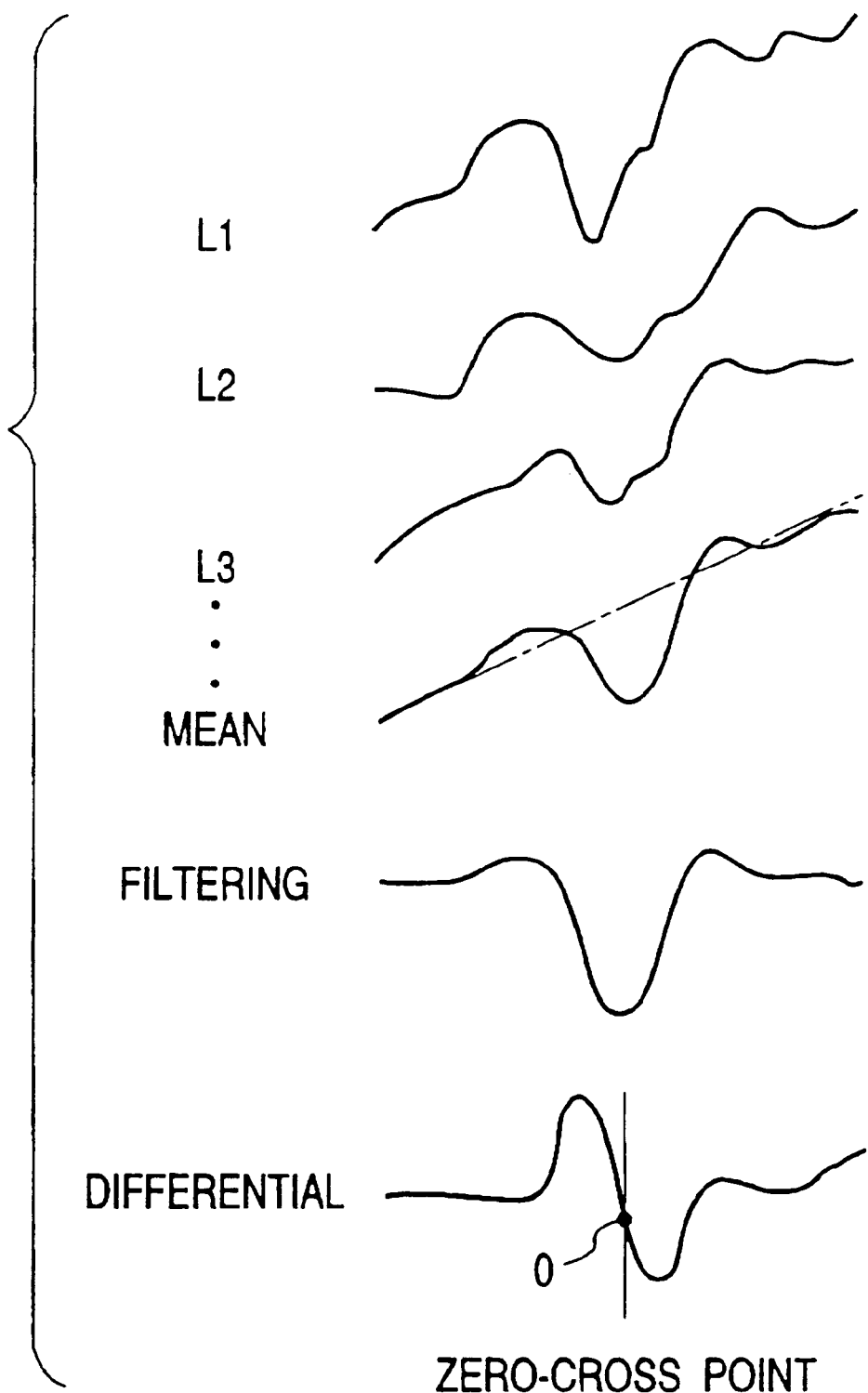
FIG. 14 is an explanatory view of signal processing.

As shown in FIG. 14, the lines L1, L2, L3, . . . are parallel to each other, and image signals of the respective line sensors are sampled in accordance with the line scanning start signals and added in the signal line buffer to average the image signals. After adding signals for one frame, an output signal from the line buffer is subjected to background correction and filtering by a low-pass filter to reduce noise. After this, a zero-cross point 0 is detected by differential processing to obtain a blood vessel position.

When the blood vessel position is compared to a predetermined tracking central position signal, the deviation amount of the blood vessel position from the tracking central position is obtained. This signal is output to the tracking control unit 129 for controlling the galvanometric mirror 115. The tracking control unit 129 drives the galvanometric mirror 115 on the basis of the signal representing the deviation amount.

Figure 15:
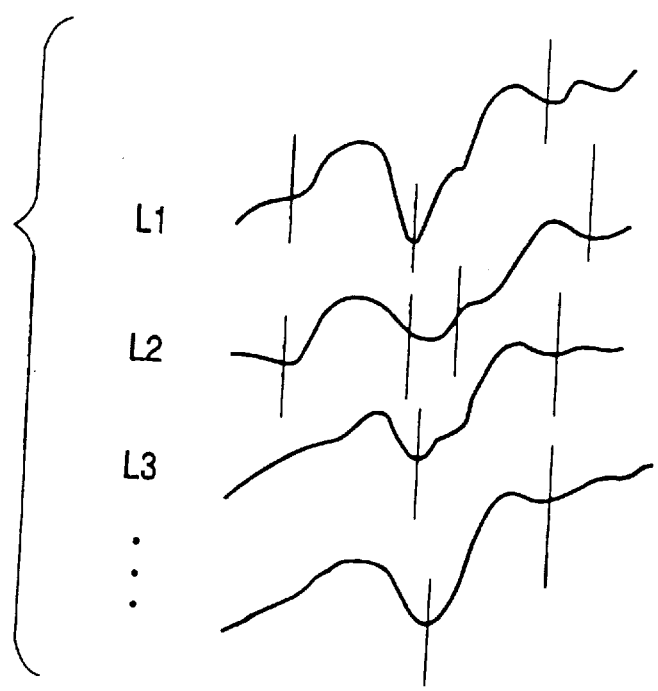
FIG. 15 is an explanatory view of signal processing.

In this embodiment, blood vessel candidate points of the lines L1, L2, L3, . . . are searched for first. The candidate points are indicated by vertical lines on the lines L1, L2, L3, . . . in FIG. 15. The candidate points correspond to zero-cross points obtained after background processing, noise removal processing, and differential processing are executed to extract a blood vessel.

Figure 16:
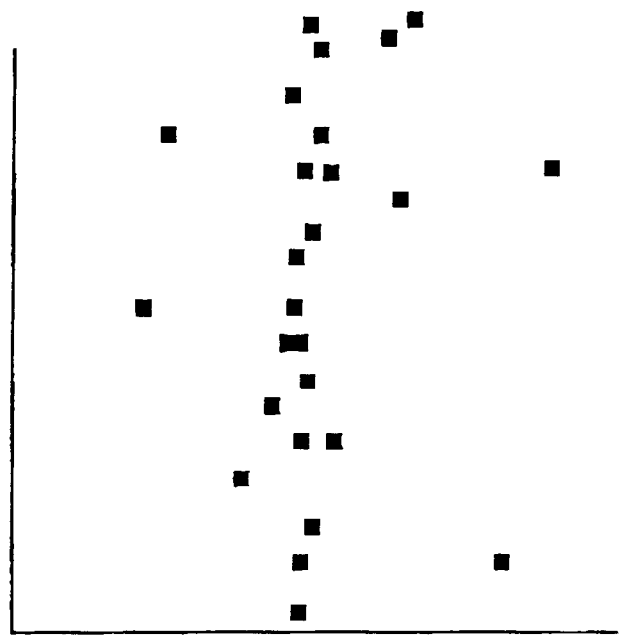
FIG. 16 is an explanatory view of signal processing.
Figure 17:
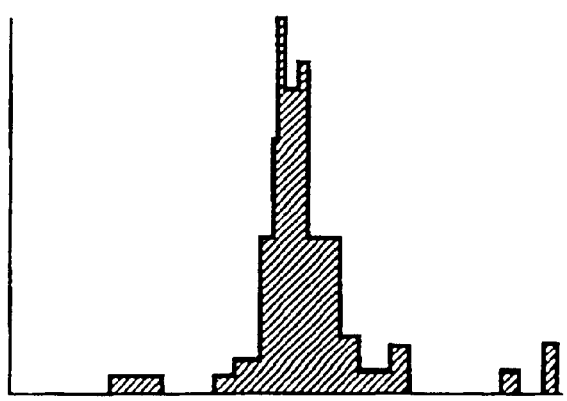
FIG. 17 is an explanatory view of signal processing.

In FIG. 16, line numbers are plotted along the ordinate, and the positions of candidate points on the lines L1, L2, L3, . . . are plotted along the abscissa. FIG. 17 shows the histogram of the candidate point positions. This histogram is plotted along the direction the blood vessel Ev runs and has a peak at the position of the blood vessel Ev to be measured. In this embodiment, this peak is detected, and the position of the blood vessel Ev is calculated from the average of positions of candidate points with a frequency 1/2 or more of the peak, thereby tracking the blood vessel as in the above embodiment.

A case wherein no other blood vessels are present in the vicinity has been described above. In this case as well, noise for each of the lines L1, L2, L3, . . . or a change in image signal due to local patterns in the blood vessel running direction is removed by adding processing in the blood vessel running direction, so only a desired blood vessel Ev can be clearly extracted.

Figure 18:
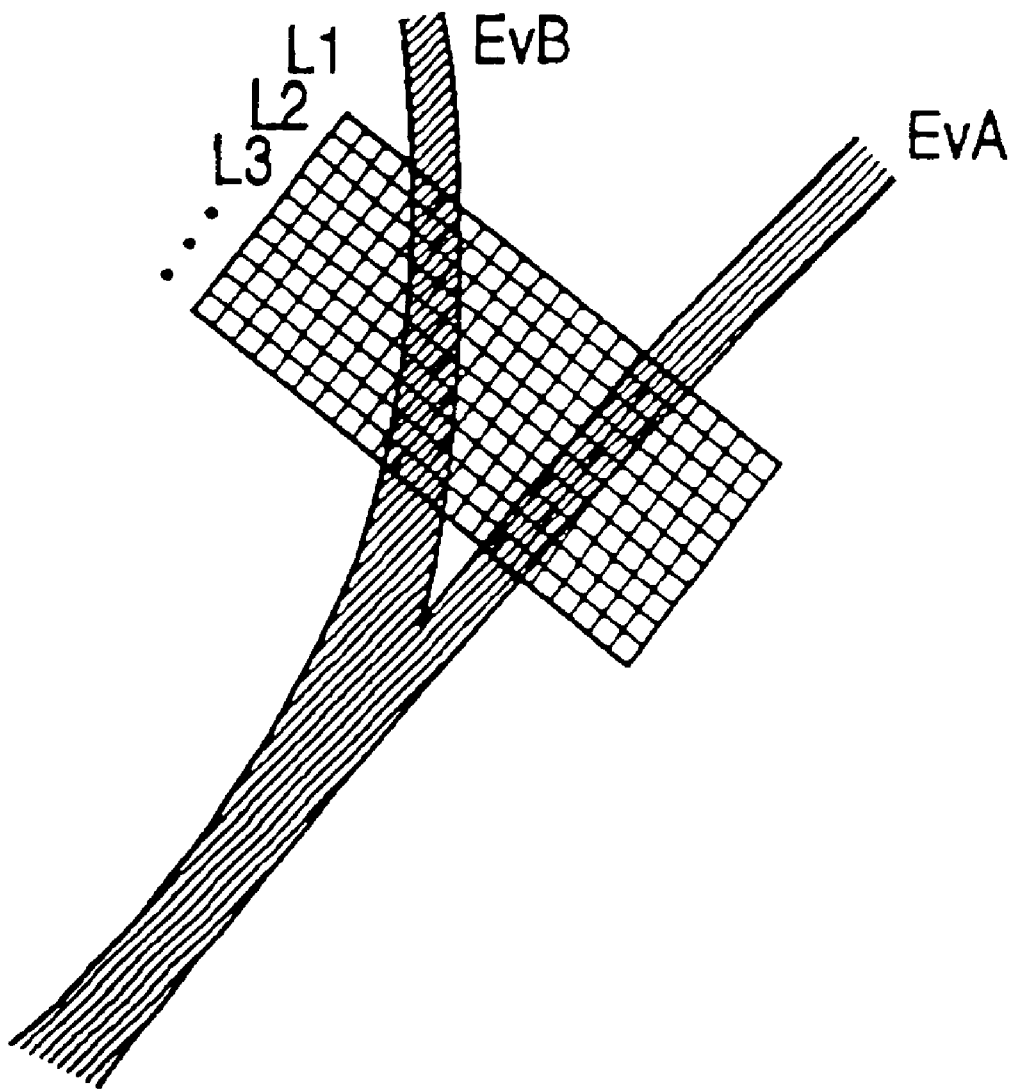
FIG. 18 is an explanatory view of the positional relationship between the image pickup element and blood vessels to be picked up.

For example, a case wherein a blood vessel EvA near a branch, which is to be tracked, has a blood vessel EvB with higher contrast in its vicinity, as shown in FIG. 18, will be described. The scanning direction of the two-dimensional image pickup element 128 is already adjusted to be perpendicular to the blood vessel running direction. For this reason, when adding processing of the lines L1, L2, L3, . . . is performed, the lower peaks representing the center of the blood vessel Ev in units of lines L1, L2, L3, . . . are at almost the same position, and an intensified signal is obtained.

Figure 19:
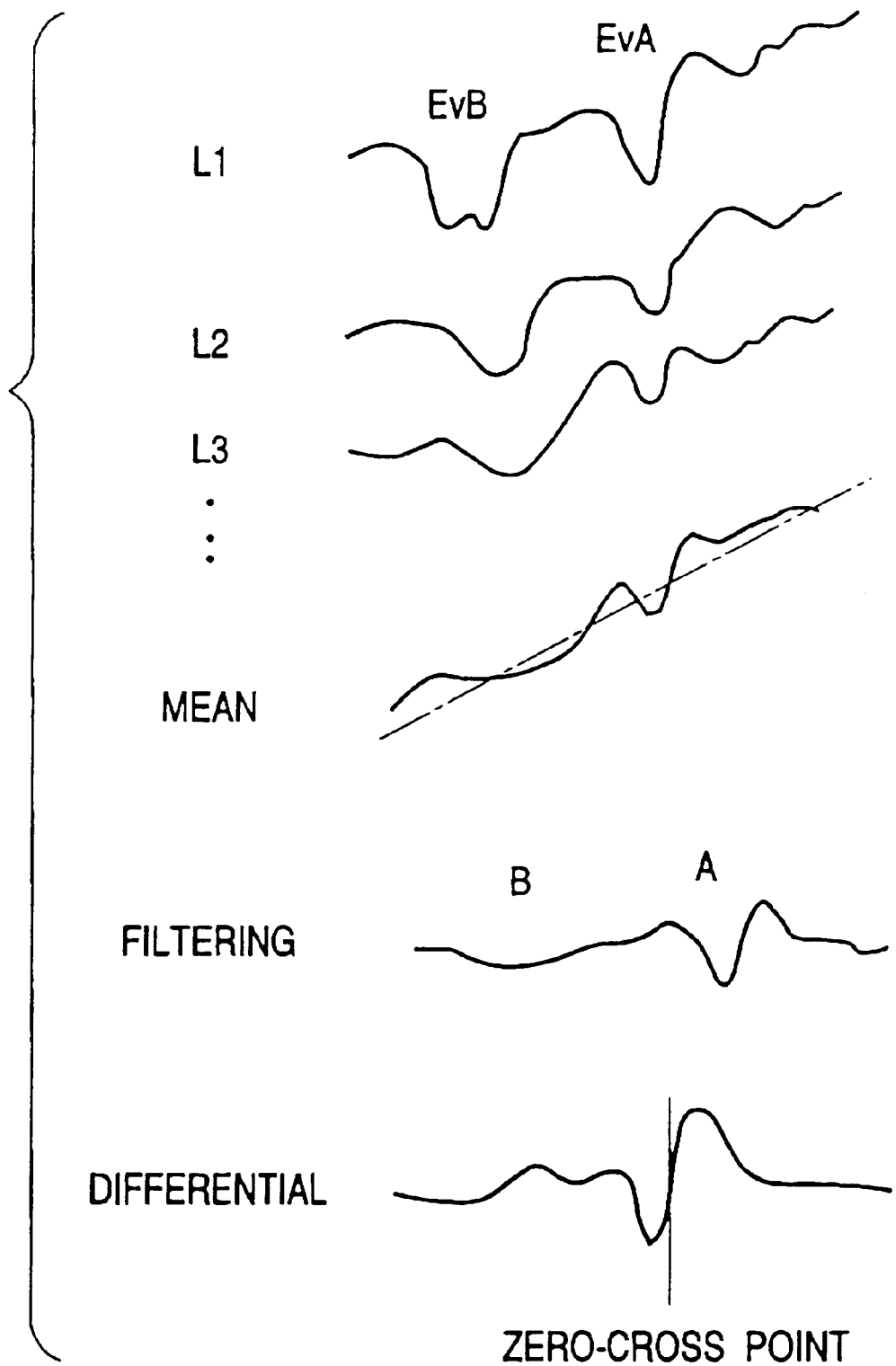
FIG. 19 is an explanatory view of signal processing.

The lower peaks of the blood vessel EvB are large in units of lines because the blood vessel is thick. However, the recessed portions are at different positions and therefore are lost in the sum signal, as shown in FIG. 19. In the signal after differential processing, the signal for the blood vessel EvA appears with a larger recessed portion, so it can be determined that the blood vessel EvA is the current object to be measured. On the basis of this signal, the tracking control unit 129 outputs the deviation amount of the blood vessel Ev to the galvanometric mirror 115.

Figure 20:
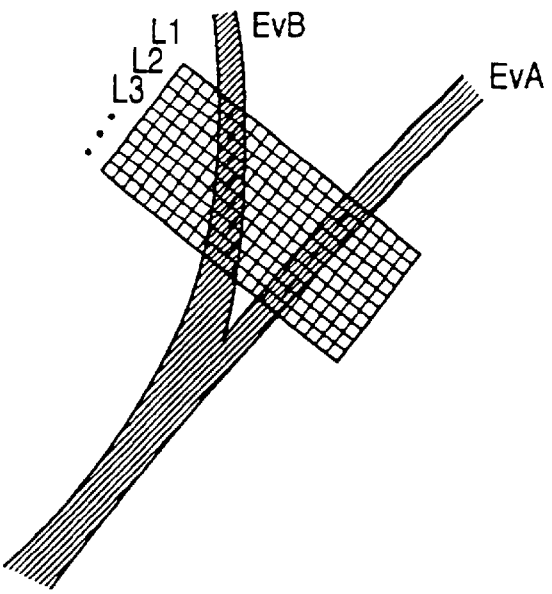
FIG. 20 is an explanatory view of the positional relationship between the image pickup element and blood vessels to be picked up.

FIG. 20 is an explanatory view of a blood vessel image signal processing method of another embodiment. An object to be measured is a blood vessel EvA for which the main scanning direction of a two-dimensional image pickup element 128 is adjusted to be perpendicular to the running direction. A blood vessel EvB is present as noise. In the above embodiment, a target blood vessel is extracted by adding image signals of lines L1, L2, L3, . . . In this embodiment, first, blood vessel candidate points of the lines L1, L2, L3, . . . are searched for.

Figure 21:
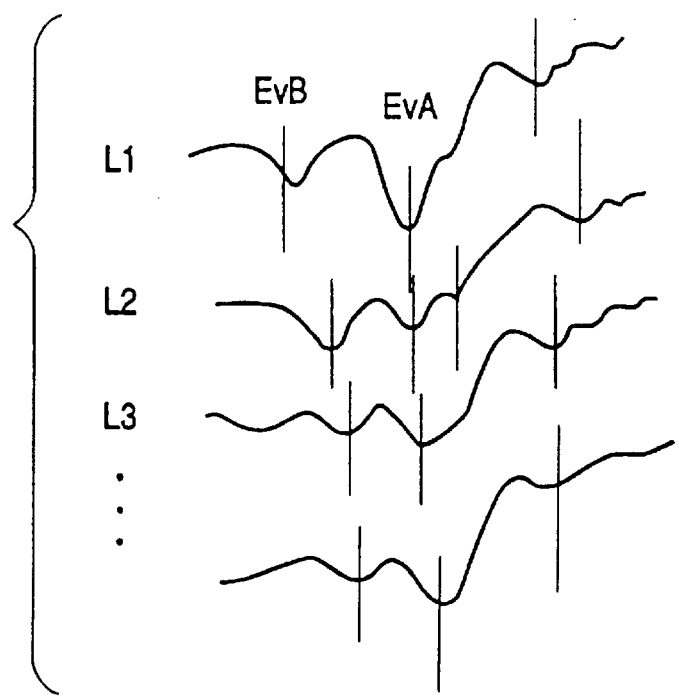
FIG. 21 is an explanatory view of signal processing.

Candidate points are indicated by vertical lines on the lines L1, L2, L3, . . . in FIG. 21. The candidate points correspond to zero-cross points obtained after background processing, noise removal processing, and differential processing are executed to extract a blood vessel in the above example.

Figure 22:
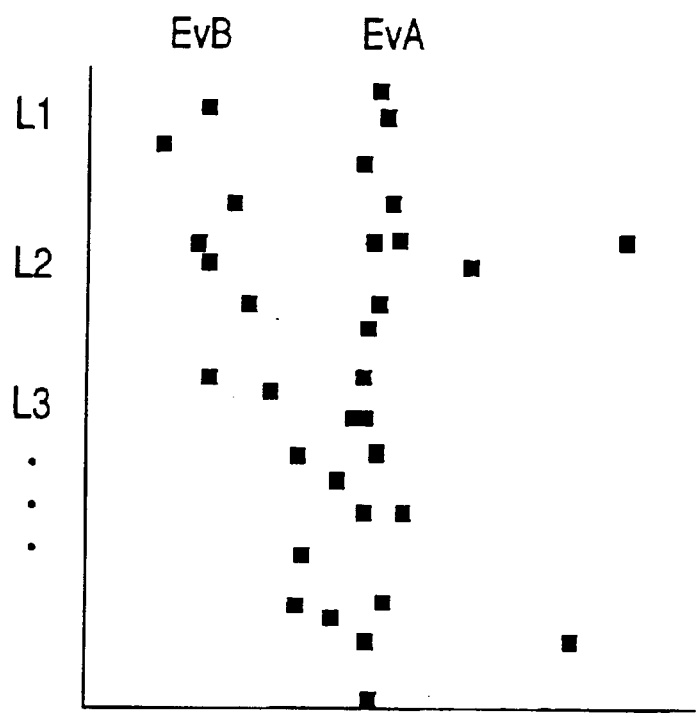
FIG. 22 is an explanatory view of signal processing.
Figure 23:
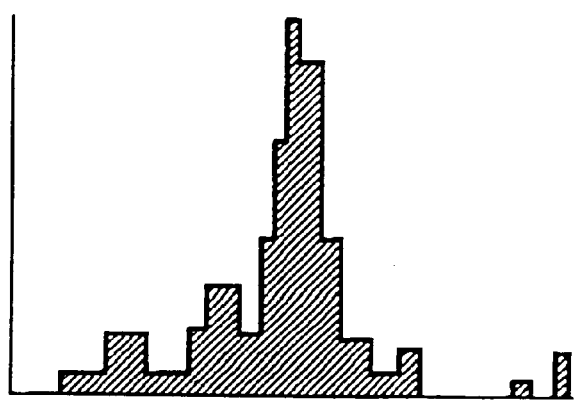
FIG. 23 is an explanatory view of signal processing.

In FIG. 22, line numbers are plotted along the ordinate, and the positions of candidate points on the lines L1, L2, L3, . . . are plotted along the abscissa. FIG. 23 shows the histogram of the candidate point positions. This histogram is plotted along the running direction of the blood vessel Ev and has a peak at the position of the target blood vessel Ev. In this embodiment, this peak is detected, and the position of the blood vessel Ev is calculated from the average of positions of candidate points with a frequency 1/2 or more of the peak, thereby tracking the blood vessel as in the above embodiment.

Figure 24:
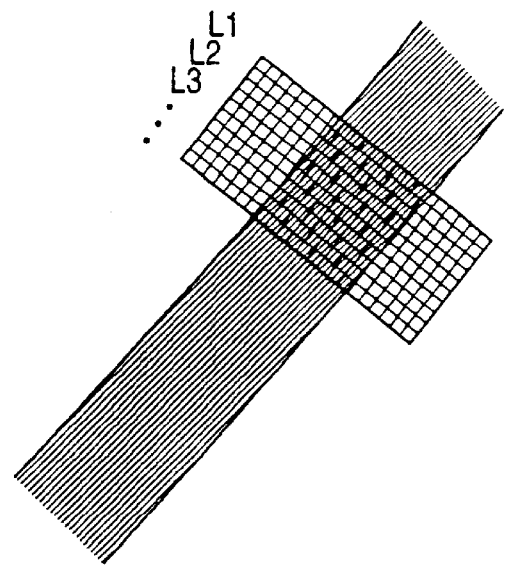
FIG. 24 is an explanatory view of the positional relationship between the image pickup element and a blood vessel to be picked up.
Figure 25:
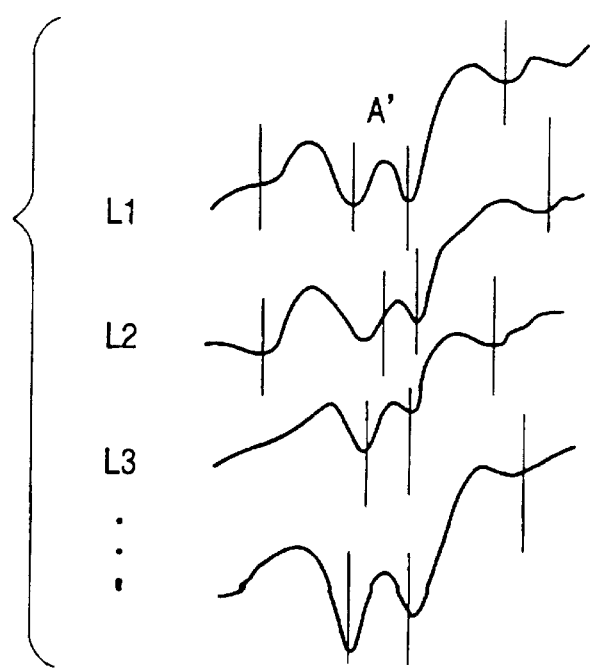
FIG. 25 is an explanatory view of signal processing.
Figure 26:
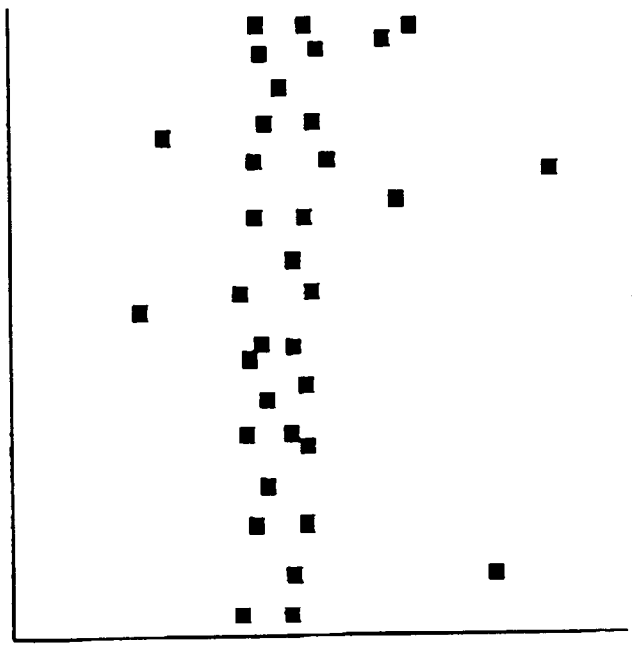
FIG. 26 is an explanatory view of signal processing.
Figure 27:
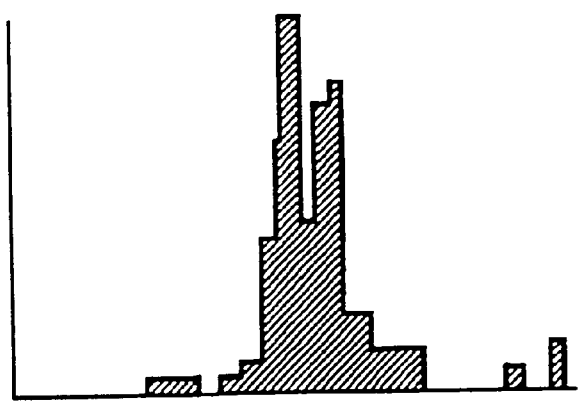
FIG. 27 is an explanatory view of signal processing.

For example, when a thick blood vessel as shown in FIG. 24 is selected as an object to be measured, regular reflection from the blood vessel wall may be observed at the blood vessel center, and an image signal may be observed as if two blood vessels were present. In this case, the same processing as described with reference to FIGS. 21 to 23 is performed as shown in FIGS. 25 to 27, and the obtained histogram draws a bimodal curve with two peaks which are close to each other and have almost the same height.

When two blood vessels are actually present, normally, one blood vessel signal is lost, as shown in FIG. 23. For this reason, even when a bimodal curve is observed, one peak becomes small. In this embodiment, for example, when each peak is within 150 μm on the fundus, and the peak height, i.e., the frequency of occurrence of the candidate point is, e.g., 30% or less, it is determined that the number of blood vessels is one, and the blood vessel central position is set in the valley between the two peaks. Otherwise, the above-described normal processing is performed with reference to the maximum peak.

In this embodiment, since the connectivity of candidate points is determined on the basis of the histogram, unlike the above-described embodiment, a blood vessel can be more accurately extracted.

Figure 28:
FIG. 28 is an explanatory view of signal processing.
Figure 29:
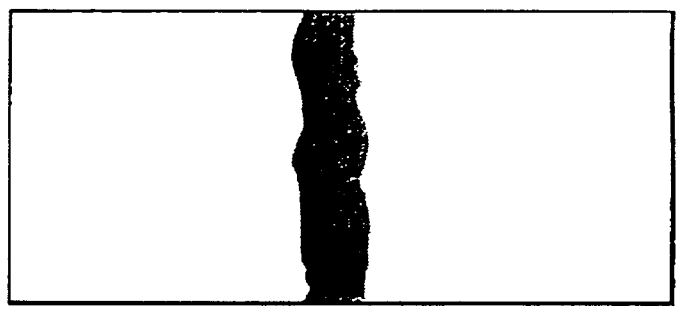
FIG. 29 is an explanatory view of signal processing.
Figure 30:
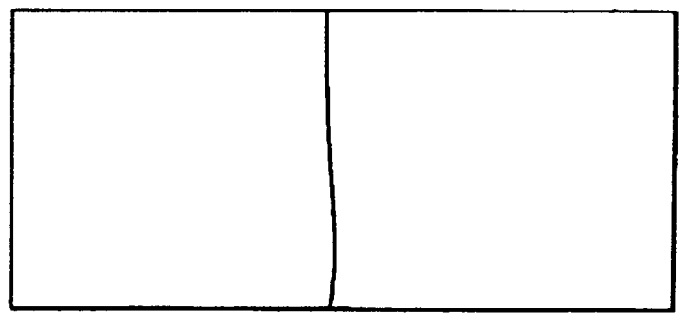
FIG. 30 is an explanatory view of signal processing.

In the above embodiment, in the processing method shown in FIGS. 28 to 30, a two-dimensional image is stored in a frame memory, and a blood vessel is extracted by two-dimensional image processing. A blood vessel image picked up as shown in FIG. 28 is subjected to two-dimensional background processing and binarized as shown in FIG. 29. After this, thinning in the horizontal direction of the page is performed to extract only connected elements in the vertical direction of the page, i.e., the blood vessel running direction. Hence, the average value of the extracted line in the horizontal direction can be used as a blood vessel position.

When the extracted line is further linearly approximated, and its slope on the screen of the two-dimensional image pickup element is detected, it can be determined whether the angle has been properly adjusted by the image rotator 114.

In the apparatus shown in the embodiment shown inn FIG. 12, the one-dimensional blood vessel tracking direction and the main scanning direction of the two-dimensional image pickup element are simultaneously adjusted to be perpendicular to the blood vessel running direction by rotating the image rotator 114. However, when this method is used, the angle relationship between the blood vessel running direction and scanning direction of the two-dimensional image pickup element 128 need not always be adjusted using the rotator 114 or the like, and the degree of freedom in designing the apparatus can be increased.

More specifically, when the blood vessel running direction is determined from the slope of the detected extracted line, and the image signal is converted in accordance with the coordinate system defined by the direction, the position of a blood vessel perpendicular to the blood vessel running direction can be obtained. This technique is well known, and a detailed description thereof will be omitted. Once the coordinate conversion coefficient is determined, the first and second signal processing can be applied as an actual signal processing method.

The above description has been made on the basis of the embodiments in which the present invention is applied to a fundus hemodromometer and, more particularly, to its tracking control unit 129. Even in blood vessel size (diameter) measurement, the same arrangement and effect as described above can be realized in association with blood vessel specification. This is different from the above embodiment only in that the blood vessel diameter is detected as information perpendicular to the blood vessel running direction, and a detailed description thereof will be omitted.

Such two-dimensional signal processing normally takes a longer time than the conventional one-dimensional signal processing. In this embodiment, however, the minimum image pickup range is set, and a practical tracking response time can be realized.

As has been described above, in the ophthalmic examination apparatus according to the present invention, in calculating blood vessel information in a direction perpendicular to the blood vessel running direction, an image signal obtained from the two-dimensional image pickup element is coded on a coordinate system having the blood vessel running direction as one axis in the first step, and then, blood vessel information is calculated in the second step. With this arrangement, more information can be used as compared to simple one-dimensional illuminance distribution, and the information can be effectively used.

More specifically, pixel outputs in the line sensor array direction are added, or blood vessel information is obtained from pixel positions which are estimated as a blood vessel in units of line sensors, thereby quickly and accurately detecting a blood vessel.

As a result, stable blood vessel information measurement is allowed, and a desired fundus blood vessel can be measured even when the contrast is low. A blood vessel having sufficient contrast can be more accurately measured, and any blood vessel detection error can be prevented. In addition, blood vessel information measurement using near-infrared light, which is conventionally impossible, can also be performed.

Extra calculation can be omitted by physically matching one scanning direction of the two-dimensional image pickup element with the blood vessel running direction. When this apparatus is applied to a blood vessel tracking system, the response speed can be increased.

In the ophthalmic examination apparatus according to the present invention, since a blood vessel image is picked up through a light deflector for tracking, an image pickup range near the target blood vessel suffices. For this reason, the number of pixels determined by the image pickup range and the required resolving power of the image pickup element for calculation can be small, and the processing time can be shortened.

What is claimed is:

1. A blood vessel detecting apparatus comprising:
   a light source for irradiating a target vessel portion with a laser beam;
   an image pickup device which picks up a blood vessel image of an eye; and
   a processing system electrically coupled to said image pickup device, the system determining the target vessel portion of the eye from the blood vessel image irradiated by the laser beam and whether the target vessel portion comprises a single blood vessel or more than a single blood vessel,
   wherein the determination of whether the target vessel portion of the eye comprises a single blood vessel or more than a single blood vessel is used to determined at least one of the blood flow velocity, diameter and blood flow volume.

2. An apparatus according to claim 1, wherein when said processing system detects specific portions on the target vessel portion that are likely to be blood vessels, and determines whether the target vessel portion comprises a single vessel or more than a single blood vessel on the basis of the distance between the specific portions.

3. An apparatus according to claim 2, wherein said processing system comprises a circuit for differentiating the output of said image pickup device, and a circuit for detecting a change in sign of signals from said differentiating circuit.

4. An apparatus according to claim 1, further comprising a deflecting optical system for deflecting a blood vessel image to project the target vessel portion on said image pickup device.

5. An apparatus according to claim 4, further comprising a measuring system for measuring the blood flow velocity in the target vessel portion.

6. An apparatus according to claim 5, wherein said measuring system comprises a light source for irradiating the target vessel portion with a laser beam and photosensors for receiving scattered light from the target vessel portion.

7. A blood vessel detecting apparatus comprising:
   a two-dimensional area sensor which picks up a two-dimensional blood vessel image of an eye in which blood flows in a blood flow direction and outputs a signal representing the two-dimensional blood vessel image; and
   a processing system that executes signal processing on the signal output by said two-dimensional area sensor to extract data representing a feature of the blood vessel, said data including at least one of the features such as the number of blood vessels, blood flow direction of the blood vessel and the position of the blood vessel on the basis of the blood vessel image picked up by said two-dimensional area sensor in a direction perpendicular to the blood flow direction.

8. An apparatus according to claim 7, wherein said feature includes information of a diameter of the blood vessel.

9. An apparatus according to claim 7, wherein said processing system integrates the output signal of said two-dimensional area sensor with respect to the blood flow direction after the extraction of data representing a feature of the blood vessel.

10. An apparatus according to claim 7, further comprising a deflecting optical system for deflecting a blood vessel image to project a target vessel portion on said two-dimensional area sensor.

11. An apparatus according to claim 7, further comprising a measuring system for measuring the blood flow velocity in the blood vessel whose image is picked up by said two-dimensional area sensor.

12. An apparatus according to claim 11, wherein said measuring system comprises a light source for irradiating the blood vessel whose image is subsequently picked up by said two-dimensional area sensor with a laser beam and photosensors for receiving scattered light from the irradiated blood vessel.

13. An apparatus according to claim 7, further comprising an image rotator which rotates the blood vessel image so as to align the blood flow direction of the blood vessel with a coordinate system of the two-dimensional area sensor.

14. A blood vessel detecting apparatus comprising:
    an image pickup device having a plurality of pixels for picking up an image of a blood vessel;
    discriminating means for discriminating the number of blood vessels on the basis of an output from said image pickup device;
    tracking means for tracking a predetermined blood vessel on the basis of information on the detected number of blood vessels; and
    velocity measuring means for measuring the velocity of the blood flowing in the blood vessel on which the tracking operation has been performed by said tracking means.

15. A blood vessel detecting apparatus comprising:
    an image pickup device having a plurality of pixels for picking up an image of a blood vessel;
    discriminating means for discriminating the number of blood vessels on the basis of an output from said image pickup device;
    diameter calculation means for calculating the diameter of a predetermined blood vessel on the basis of information of the detected number of blood vessels;
    velocity measuring means for measuring the velocity of the blood flowing in the predetermined blood vessel; and blood flow volume calculation means for calculating the blood flow volume flowing in the predetermined blood vessel on the basis of the diameter of the predetermined blood vessel and the velocity of the blood measured by said velocity measuring means.

16. A blood vessel detecting apparatus comprising:

an image pickup device having a plurality of pixels for picking up an image of a blood vessel;

discriminating means for discriminating the number of blood vessels on the basis of an output from said image pickup device;

tracking means for tracking a predetermined blood vessel on the basis of information of the discriminated number of vessels;

diameter calculation means for calculating the diameter of the predetermined blood vessel on the basis of information of the discriminated number of blood vessels;

velocity measuring means for measuring the velocity of the blood flowing in the predetermined blood vessel on which the tracking operation is performed; and blood flow volume calculation means for calculating the blood flow volume flowing in the predetermined blood vessel on the basis of the diameter of the predetermined blood vessel and the velocity of the blood measured by said velocity measuring means.

17. A blood vessel detecting apparatus comprising:

irradiation means for irradiating a target blood vessel;

image pickup means for picking up a blood vessel portion including the target blood vessel irradiated by said irradiation means to output an image pickup signal;

signal processing means for carrying out an operation on the image pickup signal as outputted;

determination means for determining whether the target blood vessel contains a single blood vessel or plural blood vessels, and a position of the target blood vessel, on the basis of the image pickup signal processed by said signal processing means; and control means for controlling a performance of said apparatus on the basis of a determination result of said determination means.

18. An apparatus according to claim 17, wherein said image pickup means comprises one-dimensional or two-dimensional CCD.

19. An apparatus according to claim 17, further comprising tracking means for tracking the target blood vessel, wherein said control means controls said tracking means to track the target blood vessel on the basis of the determination result of said determination means.

20. An apparatus according to claim 17, further comprising diameter measuring means for measuring a diameter of the target blood vessel, wherein said control means controls said diameter measuring means to measure the diameter of the target blood vessel on the basis of the determination result of said determination means.

21. An apparatus according to claims 17, 18 or 19, further comprising blood flow velocity measuring means for measuring a blood flow velocity of the target blood vessel.

* * * * *

UNITED STATES PATENT AND TRADEMARK OFFICE
CERTIFICATE OF CORRECTION

PATENT NO. : 6,569,104 B2
DATED : May 27, 2003
INVENTOR(S) : Shigeaki Ono et al.

It is certified that error appears in the above-identified patent and that said Letters Patent is hereby corrected as shown below:

<u>Title page,</u>
Item [57], ABSTRACT,
Line 5, "pixel the" should read -- the pixel --.
Item [*] Notice, insert -- This patent issued on continued prosecution application filed under 37 CFR 1.53(d), and is subject to the twenty year patent term provisions of 35 U.S.C. 154(a)(2). --

<u>Column 6,</u>
Line 1, "-1X" should read -- ⁻1x --.

<u>Column 12,</u>
Line 47, "1ximages" should read -- 1x images --.

<u>Column 16,</u>
Line 20, "inn" should read -- in --.

<u>Column 17,</u>
Line 65, "a light source for irradiating" should be deleted.
Line 66, "the target vessel portion with a laser beam and" should be deleted.

Signed and Sealed this

Twenty-seventh Day of January, 2004

JON W. DUDAS
*Acting Director of the United States Patent and Trademark Office*